US011051977B2

(12) United States Patent
Tai et al.

(10) Patent No.: US 11,051,977 B2
(45) Date of Patent: Jul. 6, 2021

(54) EYE TREATMENT DEVICE HAVING A RING LIKE SHAPE

(71) Applicants: California Institute of Technology, Pasadena, CA (US); University of Southern California, Los Angeles, CA (US)

(72) Inventors: Yu-Chong Tai, Pasadena, CA (US); Nicholas E. Scianmarello, Pasadena, CA (US); Colin A. Cook, Pasadena, CA (US); Mark S. Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 28 days.

(21) Appl. No.: 16/437,388

(22) Filed: Jun. 11, 2019

(65) Prior Publication Data

US 2019/0374381 A1 Dec. 12, 2019

Related U.S. Application Data

(60) Provisional application No. 62/683,443, filed on Jun. 11, 2018.

(51) Int. Cl.
*A61F 9/00* (2006.01)
*A61K 9/00* (2006.01)
(Continued)

(52) U.S. Cl.
CPC .......... *A61F 9/0017* (2013.01); *A61K 9/0051* (2013.01); *A61F 9/0026* (2013.01);
(Continued)

(58) Field of Classification Search
CPC .................. A61F 9/0026; A61F 9/0017; A61F 2250/0068; A61F 514/912; A61F 514/954;
(Continued)

(56) References Cited

U.S. PATENT DOCUMENTS 1,543,506 A 6/1925 Miller
3,515,095 A 6/1970 Baranow et al.
(Continued)

FOREIGN PATENT DOCUMENTS

CN 101616640 A 12/2009
WO 2008083118 A1 7/2008
(Continued)

OTHER PUBLICATIONS

U.S. Appl. No. 14/881,935 , "Non-Final Office Action", dated Aug. 7, 2017, 16 pages.
(Continued)

*Primary Examiner* — David H Willse
*Assistant Examiner* — Javier G Blanco
(74) *Attorney, Agent, or Firm* — Kilpatrick Townsend & Stockton LLP

(57) ABSTRACT

An eye treatment apparatus is described. The apparatus includes an annular body that has a hollow optical zone in its center. An inner perimeter of the annular body surrounds the optical zone. The inner perimeter has a diameter that corresponds to a diameter of the eye's cornea. An outer perimeter of the annular body has a diameter such that the annular body can extend to underneath the eye lid in an open eye position when the eye treatment apparatus is in operation. In this way, the apparatus can be worn on the eye, where the hollow optical zone substantially corresponds to the cornea and does not interfere with the field of vision. The annular body also includes a storage chamber that stores (Continued)

therapeutic liquid for an eye. An outlet is coupled with the storage chamber such that, in operation, the therapeutic liquid can be dispensed to the eye.

7 Claims, 12 Drawing Sheets

(51) Int. Cl.
G02C 7/04 (2006.01)
A61M 31/00 (2006.01)
B29D 11/00 (2006.01)
A61P 27/02 (2006.01)

(52) U.S. Cl.
CPC ... *A61F 2250/0068* (2013.01); *A61L 2430/16* (2013.01); *A61M 31/002* (2013.01); *A61P 27/02* (2018.01); *B29D 11/00096* (2013.01); *G02C 7/049* (2013.01)

(58) Field of Classification Search
CPC .......... A61F 424/427; B29D 11/00096; A61K 9/0051; G02C 7/04; A61L 2430/16; A61M 31/002; A61P 27/02
See application file for complete search history.

(56) References Cited

U.S. PATENT DOCUMENTS

| | | | |
|---|---|---|---|
| 4,572,846 | A | 2/1986 | Foss et al. |
| 4,942,018 | A | 7/1990 | Munk |
| 5,393,103 | A | 2/1995 | Cretzler |
| 5,472,436 | A | 12/1995 | Fremstad |
| 5,534,068 | A | 7/1996 | Beach et al. |
| 8,133,512 | B2 | 3/2012 | Kunzler et al. |
| 8,372,046 | B2 | 2/2013 | Meng et al. |
| 8,404,265 | B2 | 3/2013 | Chauhan et al. |
| 8,404,271 | B2 | 3/2013 | Byrne et al. |
| 8,623,400 | B2 | 1/2014 | Liu et al. |
| 8,663,194 | B2 | 3/2014 | Ambati et al. |
| 9,086,580 | B2 | 7/2015 | Grant et al. |
| 9,091,865 | B2 | 7/2015 | Hofmann et al. |
| 9,421,126 | B2 | 8/2016 | Alster et al. |
| 9,655,774 | B2 | 5/2017 | Tai et al. |
| 9,763,825 | B2 | 9/2017 | Tai et al. |
| 9,782,346 | B2 | 10/2017 | Venkatraman et al. |
| 9,937,073 | B2 | 4/2018 | de Juan, Jr. et al. |
| 10,031,348 | B2 | 7/2018 | Tai et al. |
| 10,092,387 | B2 | 10/2018 | Tai et al. |
| 2008/0035875 | A1 | 2/2008 | Tai et al. |
| 2008/0169427 | A1 | 7/2008 | Hatem et al. |
| 2008/0231799 | A1 | 9/2008 | Iuliano |
| 2008/0286338 | A1 | 11/2008 | Rosenthal et al. |
| 2010/0114309 | A1 | 5/2010 | de Juan, Jr. et al. |
| 2010/0217209 | A1 | 8/2010 | Meng et al. |
| 2011/0116035 | A1 | 5/2011 | Fritsch et al. |
| 2011/0184358 | A1 | 7/2011 | Weiner et al. |
| 2011/0282328 | A1 | 11/2011 | Ambati et al. |
| 2012/0022473 | A1 | 1/2012 | Shikamura et al. |
| 2012/0115189 | A1 | 5/2012 | Jovanovich et al. |
| 2012/0268712 | A1 | 10/2012 | Egan et al. |
| 2012/0302972 | A1 | 11/2012 | Higuchi |
| 2014/0005514 | A1 | 1/2014 | Pugh et al. |
| 2014/0193045 | A1 | 7/2014 | Otis et al. |
| 2014/0235457 | A1 | 8/2014 | Esfandyarpour et al. |
| 2015/0111023 | A1 | 4/2015 | Tai et al. |
| 2015/0293031 | A1 | 10/2015 | Fisk |
| 2016/0109726 | A1 | 4/2016 | Tai et al. |
| 2017/0001195 | A1 | 1/2017 | Unger et al. |
| 2017/0136463 | A1 | 5/2017 | Tai et al. |
| 2018/0333298 | A1 | 11/2018 | Tai et al. |

FOREIGN PATENT DOCUMENTS

| | | |
|---|---|---|
| WO | 2010041230 | 4/2010 |
| WO | 2016061125 A1 | 4/2016 |

OTHER PUBLICATIONS

U.S. Appl. No. 14/881,935 , "Notice of Allowance", dated Mar. 26, 2018, 12 pages.
U.S. Appl. No. 15/331,544 , "Final Office Action", dated Mar. 19, 2019, 35 pages.
U.S. Appl. No. 15/331,544 , "Non-Final Office Action", dated Sep. 19, 2018, 28 pages.
Arai et al., "Long-Term Electroencephalogram Measurement Using Polymer-Based Dry Microneedle Electrode", IEEE, Transducers 2015, Anchorage, Alaska, Jun. 21-25, 2015, pp. 81-84.
Chang et al., "High Yield Packaging for High-Density Multi-Channel Chip Integration of Flexible Parylene Substrate", IEEE, MEMS 2012, Paris, France, Jan. 29-Feb. 2, 2012, pp. 353-356.
Chang et al., "Packaging Study for a 512-Channel Intraocular Epiretinal Implant", IEEE, MEMS 2013, Taipei, Taiwan, Jan. 20-24, 2013, pp. 1045-1048.
EP16858334.2 , "Extended European Search Report", dated Jul. 23, 2019, 8 pages.
Kang et al., "Effects of Deposition Temperature on Parylene-C Properties", IEEE, MEMS 2013, Taipei, Taiwan, Jan. 20-24, 2013, pp. 389-392.
Kramer et al., "Polymerization of Para-Xylylene Derivatives (Parylene Polymerization). I. Deposition Kinetics for Parylene N and Parylene C", Journal of Polymer Science, Polymer Chemistry Edition, vol. 22, 1984, pp. 475-491.
Metzen et al., "Diffusion Limited Tapered Coating with Parylene C", IFMBE Proceedings 25/IX, 2009, pp. 96-97.
Metzen et al., "Diffusion-Limited Deposition of Parylene C", Journal of Microelectromechanical Systems, vol. 20, No. 1, Feb. 2011, pp. 239-250.
PCT/US2016/058200 , "International Preliminary Report on Patentability", dated May 3, 2018, 12 pages.
PCT/US2016/058200 , "International Search Report and Written Opinion", dated Jan. 10, 2017, 13 pages.
PCT/US2019/033369 , "International Search Report and Written Opinion", dated Sep. 17, 2019, 11 pages.
PCT/US2019/033369 , "Invitation to Pay Additional Fees and, Where Applicable, Protest Fee", dated Jul. 3, 2019, 2 pages.
PCT/US2019/036498 , "Invitation to Pay Additional Fees and, Where Applicable, Protest Fee", dated Aug. 19, 2019, 2 pages.
Ramachandran et al., "A Study of Parylene C Polymer Deposition Inside Microscale Gaps", IEEE Transactions on Advanced Packaging, vol. 30, No. 4, Nov. 2007, pp. 712-724.
Sawano et al., "Sealing Method of PDMS as Elastic Material for MEMS", IEEE, MEMS 2008, Tucson, Arizona, Jan. 13-17, 2008, pp. 419-422.
Senkevich et al., "Thermomechanical Properties of Parylene X, A Room-Temperature Chemical Vapor Depositable Crosslinkable Polymer", Chemical Vapor Deposition, vol. 13, 2007, pp. 55-59.
Wang et al., "Reliable Deposition of Ultra-Thin Parylene", IEEE 2016, MEMS 2016, Shanghai,China, Jan. 24-28, 2016, pp. 462-464.
PCT/US2015/055368, "International Preliminary Report on Patentability", dated Apr. 27, 2017, 10 pages.
PCT/US2015/055368, "International Search Report and Written Opinion", dated Feb. 16, 2016, 12 pages.
"Compliance Problems with Glaucoma Eye Drops," OpthalmologyWeb, available https://www.ophthalmologyweb.com/Featured-Articles/19875-Compliance-Problems-with-Glaucoma-Eye-Drops/, published Aug. 23, 2010, 3 pages.
"Improving compliance through access to eye drop medication," available https://www.cameron-graham.co.uk/pages/pharmacists.php, accessed Jun. 14, 2019.
"The role of the pharmacists in improving glaucoma compliance," NI Pharmacy in Focus, available https://www.cameron-graham.co.uk/pages/pharmacists.php, Aug. 2005, accessed Jun. 14, 2019.

(56) References Cited

OTHER PUBLICATIONS

Robin, Alan L., Beyond Compliance-Getting the Drops in, *Review of Ophthalmology*, Feb. 18, 2010, 5 pages, available https://reviewofophthalmology.com/article/beyond-compliance-getting-the-drops-in.

"How to succeed at eye drop treatment: It's all in your hands," Johns Hopkins Medicine, Glaucoma Center of Excellence, 7 pages, available https://www.hopkinsmedicine.org/wilmer/services/glaucoma/book/chapter_how_to_succeed_with_drops.html, accessed Jun. 14, 2019.

PCT/US2019/033369, "International Preliminary Report on Patentability", dated Dec. 3, 2020, 8 pages.

PCT/US2019/036498, "International Preliminary Report on Patentability", dated Dec. 24, 2020, 9 pages.

U.S. Appl. No. 16/017,667, "Non-Final Office Action", dated Nov. 15, 2019, 18 pages.

PCT/US2019/036498, "International Search Report and Written Opinion", dated Oct. 31, 2019, 12 pages.

EYE TREATMENT DEVICE HAVING A RING LIKE SHAPE

CROSS-REFERENCES TO RELATED APPLICATIONS

This application claims the benefit of U.S. Provisional Application No. 62/683,443, filed Jun. 11, 2018, the contents of which are hereby incorporated in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

Generally, embodiments of the present invention relate to devices for administration of a therapeutic agent (e.g., medicament, drugs, saline, etc.) to a particular part of a patient's body. One example of targeted delivery to a part of a patient's body is the eye.

The most common treatment for various eye conditions is through topical application of ophthalmic solutions or eye drops. This method of fluid delivery to the eye accounts for 90% of all the ophthalmic medications. This mode of delivery, however, is very inefficient, with sometimes less than 10% absorption in the eye of the medicine from the eye drops.

Furthermore, compliance in eye drop delivery is a major issue in ophthalmology. In particular, non-compliance is a well-cited issue with glaucoma medication with 25% of patients never filling their second prescription. Even when remembering to apply an eye-drop many patients fail to do so properly by failing to instill the drop in the eye, and fail to dispense the appropriate amount of solution. Further failure to instill the eye drop properly or at all can eventually lead to optic nerve damage and eventually irreversible blindness. Short of surgical intervention there is little treatment for glaucoma, and so it is relevant that patients get the appropriate dose consistently.

Existing nonsurgical, long-term methods to apply topical medication to the eye are typically not adequate. While there are patents detailing some mechanisms for drug pumps, they fall short of dispensing the such medication consistently. It would be beneficial to deliver ophthalmic fluids and medications more precisely and effectively.

As such, there is a need in the art for improved approaches to targeted drug delivery in at least a patient's eye.

BRIEF SUMMARY

Eye treatment apparatuses are described herein. In an example, an eye treatment apparatus wearable on a sclera of an eye includes an annular body defining a hollow optical zone. The annular body is defined by an inner perimeter, an outer perimeter that surrounds the inner perimeter, a top surface between the inner perimeter and the outer perimeter, and a bottom surface opposite the top surface. The inner perimeter surrounds the hollow optical zone. A shortest distance between two opposite points of the inner perimeter is between eight and twelve millimeters. The eye treatment apparatus also includes a therapeutic liquid storage chamber disposed within the annular body. The eye treatment apparatus also includes a therapeutic liquid outlet coupled with the therapeutic liquid storage chamber and disposed within the inner perimeter, the outer perimeter, or the bottom surface. The eye treatment apparatus also includes a pressure chamber disposed within the annular body.

In an example, the eye treatment apparatus further includes a flexible diaphragm disposed between the pressure chamber and the therapeutic liquid storage chamber.

In an example, the therapeutic liquid storage chamber comprises a therapeutic liquid. The eye treatment apparatus further includes further a movable barrier disposed between the pressure chamber and the therapeutic liquid.

In an example, the therapeutic liquid storage chamber comprises a therapeutic liquid for an eye. the inner perimeter is centered around a center of the hollow optical zone. The outer perimeter is centered around the center of the hollow optical zone and has a diameter between twenty and one hundred millimeters.

In an example, the inner perimeter includes one or more flaps.

In an example, the inner perimeter is shaped as a non-continuous circle centered around a center of the hollow optical zone and has a diameter between eight and twelve millimeters.

In an example, the bottom surface is a stiction surface. The eye treatment apparatus further includes a tether connected to the stiction surface and comprising suture holes.

In an example, the pressure chamber comprises a plurality of bio safe chemicals that are separated by at least one seal. In a further example, the pressure chamber further includes a pressure source formed with a frangible material. The pressure source includes a first chemical storage chamber and a second chemical storage chamber separated from each other by the seal. The first chemical storage chamber contains a first bio safe chemical. The second chemical storage chamber contains a second bio safe chemical.

In an example, the pressure chamber comprises a bio safe phase changing material.

In an example, the eye treatment apparatus further includes a plurality of therapeutic liquid storage chambers, each of the plurality of therapeutic liquid storage chambers coupled with the therapeutic liquid outlet.

In an example, the eye treatment apparatus further includes a plurality of therapeutic liquid storage chambers and a plurality of therapeutic liquid outlets, each of the plurality of therapeutic liquid storage chambers coupled with a separate one of the plurality of therapeutic liquid outlets.

In an example, the eye treatment apparatus further includes a plurality of therapeutic liquid outlets, each of the plurality of therapeutic liquid outlets coupled with the therapeutic liquid storage chamber.

In an example, the eye treatment apparatus further includes a plurality of pressure chambers and a plurality of flexible membranes, each of the plurality of flexible membranes disposed between the therapeutic liquid storage chamber and a separate one of the plurality of pressure chambers.

In an example, the eye treatment apparatus further includes a plurality of therapeutic liquid storage chambers, a plurality of pressure chambers, and a plurality of flexible membranes, each of the plurality of flexible membranes disposed between a separate of the plurality of therapeutic liquid storage chambers and a separate one of the plurality of pressure chambers.

In an example, the eye treatment apparatus further includes a pillar having one end attached to the bottom surface and an opposite end attached to the top surface.

In an example, the eye treatment apparatus further includes a delivery channel having one end connected to the therapeutic liquid storage chamber and an opposite end connected to the therapeutic liquid outlet. In a further example, the eye treatment apparatus further includes a one way valve disposed within the delivery channel or the therapeutic liquid outlet. In another example, the eye treatment apparatus further includes a flow restrictor disposed within or connected to the delivery channel or the therapeutic liquid outlet.

In an example, an eye treatment apparatus wearable on a sclera of an eye includes an annular body defining a hollow optical zone. The annular body is defined by an inner perimeter, an outer perimeter that surrounds the inner perimeter, a top surface between the inner perimeter and the outer perimeter, and a bottom surface opposite the top surface. The inner perimeter surrounds the hollow optical zone. A shortest distance between two opposite points of the inner perimeter is between eight and twelve millimeters. The eye treatment apparatus also includes a therapeutic liquid storage chamber disposed within the annular body. The eye treatment apparatus also includes a therapeutic liquid outlet coupled with the therapeutic liquid storage chamber and disposed within the inner perimeter, the outer perimeter, or the bottom surface. The eye treatment apparatus also includes a one way inlet valve coupled with the therapeutic liquid storage chamber and having an outlet port directed inward to the therapeutic liquid storage chamber.

In an example, the therapeutic liquid storage chamber comprises a therapeutic liquid for an eye. The inner perimeter is centered around a center of the hollow optical zone. The outer perimeter is centered around the center of the hollow optical zone and has a diameter between twenty and one hundred millimeters.

In an example, the eye treatment apparatus further includes a one way outlet valve coupled with the therapeutic liquid storage chamber and having an outlet port directed outward from the therapeutic liquid storage chamber. In a further example, the one way outlet valve is disposed within the therapeutic liquid outlet or a delivery channel between the therapeutic liquid outlet and the therapeutic liquid storage chamber. In another example, the one way outlet valve is connected to an output port of the therapeutic liquid storage chamber.

In an example, the w one way inlet valve is connected to an input port of the therapeutic liquid storage chamber.

In an example, the eye treatment apparatus further includes a replenishment chamber storing a liquid or a gas. In a further example, the one way inlet valve is disposed between the replenishment chamber and the therapeutic liquid storage chamber.

In an example, an eye treatment apparatus wearable on a sclera of an eye includes an annular body defining a hollow optical zone. The annular body is defined by an inner perimeter, an outer perimeter that surrounds the inner perimeter, a top surface between the inner perimeter and the outer perimeter, and a bottom surface opposite the top surface. The inner perimeter surrounds the hollow optical zone. A shortest distance between two opposite points of the inner perimeter is between eight and twelve millimeters. The eye treatment apparatus also includes a therapeutic liquid delivery channel disposed within the annular body and having a cross section. The eye treatment apparatus also includes a therapeutic liquid outlet coupled with the therapeutic liquid delivery channel and disposed within the inner perimeter, the outer perimeter, or the bottom surface. The eye treatment apparatus also includes a pressure chamber disposed within the annular body and coupled with the therapeutic liquid delivery channel. The eye treatment apparatus also includes a movable barrier disposed within the therapeutic liquid delivery channel. The movable barrier has the cross section. An end of the movable barrier is directed toward the pressure chamber.

In an example, the therapeutic liquid delivery channel comprises a therapeutic liquid for an eye. The inner perimeter is centered around a center of the hollow optical zone. The outer perimeter is centered around the center of the hollow optical zone and has a diameter between twenty and one hundred millimeters.

In an example, one end of the therapeutic liquid delivery channel is connected to the pressure chamber. Another end of the therapeutic liquid delivery channel is connected to the therapeutic liquid outlet.

In an example, a first portion of the therapeutic liquid delivery channel contains a therapeutic liquid for an eye. The pressure chamber includes a second portion of the therapeutic liquid delivery channel. The movable barrier is disposed between the first portion and the second portion.

In an example, the movable barrier is a solid object or a liquid having a viscosity over a predefined viscosity threshold.

In an example, an opposite end of the movable barrier is directed toward the therapeutic liquid outlet.

In an example, the eye treatment apparatus further includes a flow restrictor disposed within or connected to the therapeutic liquid delivery channel or the therapeutic liquid outlet.

A further understanding of the nature and the advantages of the embodiments disclosed and suggested herein may be realized by reference to the remaining portions of the specification and the attached drawings.

DETAILED DESCRIPTION

Figure 1:
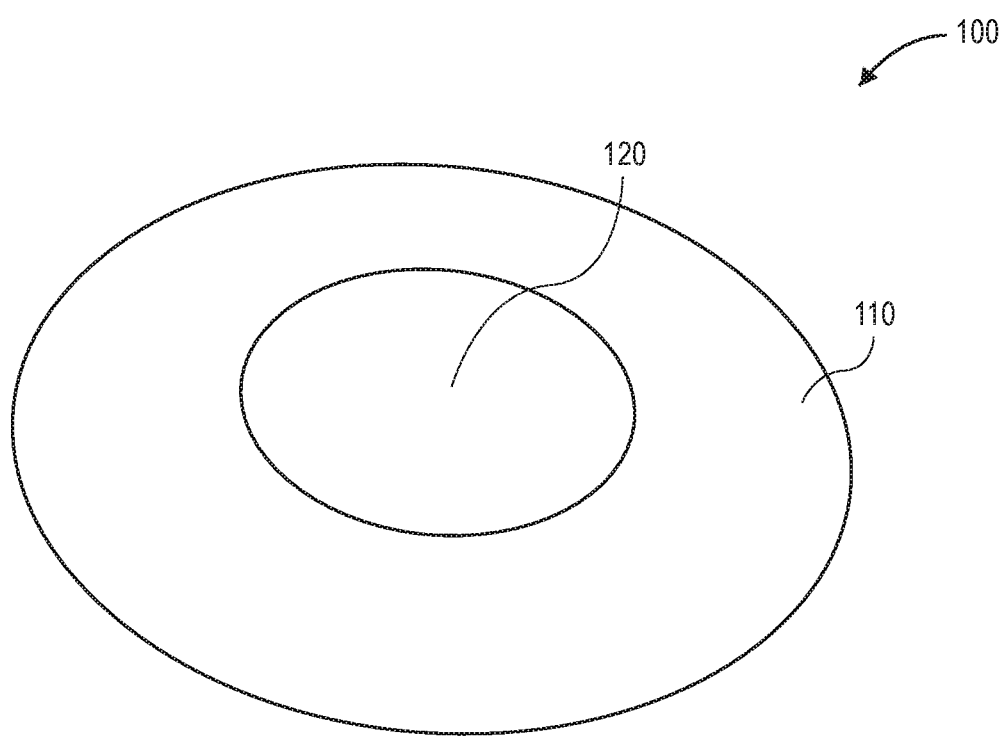
FIG. 1 illustrates a perspective view of an example ophthalmic liquid delivery ring in accordance with an embodiment.

Generally, eye treatment apparatuses are described herein. Particularly described are exemplary eye treatment apparatuses, each wearable on a sclera of an eye, having a ring like shape, and usable to treat dry different conditions of the eye. Each of the eye treatment apparatuses dispenses a reliable amount of liquid to the eye over extended periods of time. The particular type and amount of liquid and the particular rate and location of the liquid's delivery can depend on the condition of the eye, whereby an eye treatment device is configured to contain the particular type and amount of liquid and to dispense the liquid at the particular location according to the particular rate.

In embodiments, an eye treatment apparatus includes an annular body that has a hollow optical zone in its center. An inner perimeter of the annular body surrounds the optical zone. The annular body also includes an outer perimeter, a top surface, and a bottom surface. The inner and outer parameters are defined according to concentric circles centered around the center of the optical zone. The inner perimeter has a diameter that corresponds to a diameter of the eye's cornea. The outer perimeter has a diameter such that the annular body can extend to underneath the eye lid in an open eye position when the eye treatment apparatus is in operation. In this way, the eye treatment apparatus can be worn on the eye, with the top surface facing outwardly from the eye and the bottom surface in contact with the eye. The hollow optical zone substantially corresponds to the cornea and does not interfere with (e.g., block) the field of vision.

Furthermore, the annular body includes a therapeutic liquid storage chamber that forms a reservoir storing therapeutic liquid for an eye, such as a drug for treating a condition of the eye. A therapeutic liquid outlet is coupled with the therapeutic liquid storage chamber such that, in operation, the therapeutic liquid can flow from the reservoir storing therapeutic and be dispensed from the therapeutic liquid outlet. The location of the therapeutic liquid outlet depends on the condition to treat and can be disposed within the inner perimeter, the outer perimeter, or the bottom surface of the annular body. In addition, a flow restrictor can be disposed between the therapeutic liquid outlet and the therapeutic liquid storage chamber, within therapeutic liquid outlet, or within an output port of the therapeutic liquid storage chamber to restrict the flow of the therapeutic liquid according to a targeted flow rate.

Different configurations are possible to drive the flow of the therapeutic liquid. In one example configuration, the annular body also includes a pressure chamber and a flexible membrane disposed between the pressure chamber and the therapeutic liquid storage chamber. Pressure inside the pressure chamber can be generated based on chemical decomposition or a phase change, where this pressure actuates the flexible membrane, and where the actuation causes the flow of the therapeutic liquid from the therapeutic liquid storage chamber. In another example configuration, the therapeutic liquid storage chamber includes a delivery channel, such as a spiral delivery channel. The delivery channel contains a therapeutic liquid. A movable membrane is disposed within the delivery channel and has substantially the same cross section of the delivery channel. One end of the movable membrane is directed toward a pressure chamber of the annular body. In operation, pressure from the pressure chamber pushes the movable membrane along the delivery channel and toward the therapeutic liquid outlet, thereby causing the flow of the therapeutic liquid from the delivery channel to the therapeutic liquid outlet. In yet another example configuration, the annular body does not include an internal pressure source. Instead, external pressure is used to cause the flow during operation. The external pressure can be pressure from the eyelid or pressure from a finger push over the eye lid and onto the annular body. In this example, the annular body includes a one way inlet valve coupled with the therapeutic liquid storage chamber and having an outlet port directed inward to the therapeutic liquid storage chamber. In this way, at the end of the pressure application and as the pressure is being released, the one way inlet valve is activated to release liquid or gas into the therapeutic liquid storage chamber for pressure equalization. These and other aspects of the embodiments are further described in connection with the next figures.

FIG. 1 illustrates a perspective view of an example ophthalmic liquid delivery ring 100 in accordance with an embodiment. The ophthalmic liquid delivery ring 100 is an example of an eye treatment apparatus.

In an example, the ophthalmic liquid delivery ring 100 include an annular body 110. The annular body 110 has a hollow optical zone 120 that is centered around the center of the annular body 110. The hollow optical zone 120 is empty and does not block, alter, or interfere with a field of vision of an eye once the ophthalmic liquid delivery ring 100 is worn on the eye. For example, the hollow optical zone 120 has a circular shape with a diameter that is proximate to the average diameter of the human eye's cornea. For instance, this diameter is in the range of eight to twelve millimeters. In a specific example, the diameter is ten millimeters or about ten millimeters.

The annular body 110 has an inner parameter that surrounds or is around the hollow optical zone 120. In this case, the inner perimeter can also have circular shape with a diameter that is proximate to the average diameter of the human eye's cornea. For instance, this diameter is in the range of eight to twelve millimeters. In a specific example, the diameter is ten millimeters or about ten millimeters. When worn on the eye, the inner perimeter can be located at the edge of or proximate to the cornea.

An outer perimeter is opposite to the inner parameter. The outer perimeter can also have circular shape. In operation, the outer perimeter can be located on the sclera. In one specific example, the outer perimeter can be under the eye lid when the eye is in an open position. In an illustration, the circular shape of the outer perimeter has a diameter that is in the range of twenty to one hundred millimeters. In a specific example, the diameter is sixty millimeters or about sixty millimeters.

The annular body 110 can have curvature that generally follows the curvature of the sclera. Different materials are available to make the annular body 110. For instance, annular body 110 can be made out of any or a combination of rigid permeable glass, silicone, parylene or any other bio safe flexible material suitable for being worn on the eye and that can be formed into the curvature.

Accordingly, the ophthalmic liquid delivery ring 100 has ring like shape with its hollow optical zone 120 being about the size of the average human's cornea and its outer perimeter being large enough to fall on the sclera. When worn on the eye, the ophthalmic liquid delivery ring 100 does not cover the cornea, but extends from the cornea over the sclera and possibly to under the eyelid. By fact of its size and position, the ophthalmic liquid delivery ring 100 should easily be retained on the eye without needing to worry about moisture content, suction, or capillary forces. This allows the ophthalmic liquid delivery ring 100 to be useful in a variety of patients, including those who suffer dry eyes, and would allow us to fit drug quantities in the range of one hundred μL into such an apparatus, thereby allowing for long term wear (e.g., two to six months).

Depending on the pressure-related configuration of the ophthalmic liquid delivery ring 100, as further described in connection with the next figures, the ophthalmic liquid delivery ring 100 can be configured as a no power or low power pump designed into a scleral ring (e.g., a contact lens with an open central optical section), that encompasses all or part of the sclera. Although various embodiments describe an ophthalmic liquid delivery ring as having a center optical zone that is hollow, variations to the optical zone are possible. For instance, the optical zone can include transparent material (e.g., glass) or a contact lens (e.g., one for vision correction).

Although various embodiment of the present discloser are described in connection with an inner perimeter that has a circular shape with a diameter between eight and twelve millimeters, the embodiments of the present disclosure are not limited as such. Instead, other shapes and dimensions of the inner perimeter are possible. For example, it is sufficient for the inner perimeter to surround the hollow optical zone 120 (e.g., fully or partially while being outside of the optical the hollow optical zone 120), where different shapes and dimensions can be used. The inner parameter can have opposite sides relative to the center of the hollow optical zone 120. Two points on two opposite sides are referred to herein as opposite points. A shortest distance between two opposite points of the inner perimeter should be equal to or larger than width and length of the hollow optical zone 120. For instance, the shortest distance is in the range of eight to twelve millimeters. In a specific example, the shortest distance is ten millimeters or about ten millimeters.

Furthermore, although various embodiment of the present discloser are described in connection with an a hollow optical zone that has a circular shape with a diameter between eight and twelve millimeters, the embodiments of the present disclosure are not limited as such. Instead, other shapes and dimensions of the hollow optical zone are possible. For example, it is sufficient for the hollow optical zone to be large enough not to occlude or interface with a field of view of an eye. In an example, the hollow optical zone can be circular to mimic the eye's cornea and can have a diameter equal to a larger than the average size of the cornea (e.g., the diameter is in the range of eight to twelve millimeters. In a specific example, this diameter is ten millimeters or about ten millimeters). In another example, the hollow optical zone can be circular but encroach on the cornea while having a diameter larger than the average size of the eye's pupil in the dilated state (e.g., four to eight millimeters). In yet another example, the hollow optical zone need not be circular. For instance, the hollow optical zone can have a center and opposite sides relative to the center (e.g., such as in the case of a circle, a rectangle, a square, a triangle or any other shape including a random shape). A shortest distance between two opposite points of the hollow optical zone should be equal to or larger than the average size of the cornea (or, alternatively, the pupil in the dilated state). For instance, the shortest distance is in the range of eight to twelve millimeters (or alternatively in the range of four to eight to eight millimeters; or collectively in the range of four to twelve millimeters). In a specific example, the shortest distance is ten millimeters or about ten millimeters.

Figure 2:
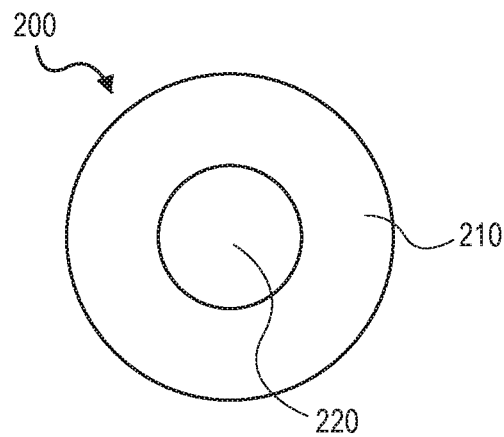
FIG. 2 illustrates a top view of an example ophthalmic liquid delivery ring that is defined based on concentric circles in accordance with an embodiment.

FIG. 2 illustrates a top view of an example ophthalmic liquid delivery ring 200 that is defined based on concentric circles in accordance with an embodiment. The ophthalmic liquid delivery ring 200 is an example of the ophthalmic liquid delivery ring 100 of FIG. 1.

In an example, the ophthalmic liquid delivery ring 200 includes an annular body 210 and an optical zone 220. The optical zone 220 is at the center of the annular body 210 and is hollow. As illustrated, the optical zone 220 has a circular shape with a diameter in the range of eight to twelve millimeters (e.g., two opposite points of the optical zone 220 are found on opposite ends of the circle, and the shortest distance between the two opposite points is in the range of eight to twelve millimeters; in a specific example, the shortest distance is ten millimeters or about ten millimeters). An inner perimeter of the annular body 210 is also circular and is around the optical zone 220 and, thus, has the same diameter (e.g., two opposite points of the inner perimeter are found on opposite ends of the circle, and the shortest distance between the two opposite points is in the range of eight to twelve millimeters; in a specific example, the shortest distance is ten millimeters or about ten millimeters; the two opposite points of the inner perimeter can correspond to the two opposite points of the optical zone 220). An outer perimeter of the annular body 210 has also a circular shape with a diameter in the range of twenty to one hundred millimeters. Accordingly, the inner perimeter and the optical zone 220 are defined relative to an inner circle that has a diameter between eight and twelve millimeters. In comparison, the outer perimeter is defined relative to an outer circle that has a diameter between twenty and one hundred millimeters. The inner circle and the outer circle are continuous and concentric. The center of these two circles is the center of the annular body 210 and the optical zone 220.

Figure 3:
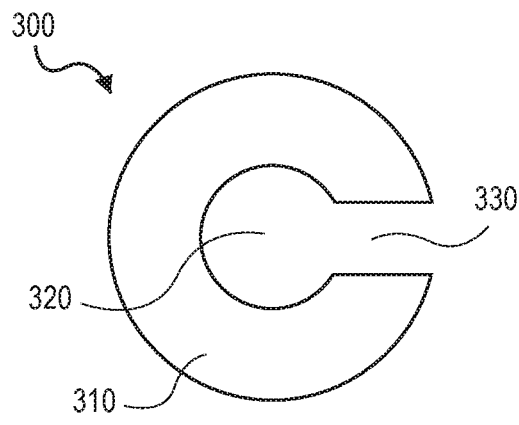
FIG. 3 illustrates a top view of another example ophthalmic liquid delivery ring that is defined based on non-continuous concentric circles in accordance with an embodiment.

FIG. 3 illustrates a top view of another example ophthalmic liquid delivery ring 300 that is defined based on non-continuous concentric circles in accordance with an embodiment. The ophthalmic liquid delivery ring 300 is an example of the ophthalmic liquid delivery ring 100 of FIG. 1.

In an example, the ophthalmic liquid delivery ring 300 includes an annular body 310 and an optical zone 320. The optical zone 320 is at the center of the annular body 310 and is hollow. Similarly to the ophthalmic liquid delivery ring 200 of FIG. 2, the ophthalmic liquid delivery ring 300 has an inner perimeter and an outer perimeter, where the inner perimeter and the optical zone 320 are defined relative to an inner circle that has a diameter between eight and twelve millimeters, where the outer perimeter is defined relative to an outer circle that has a diameter between twenty and one hundred millimeters, and where the inner circle and the outer circle are concentric. However, and unlike the ophthalmic liquid delivery ring 200 of FIG. 2, the inner circle and the outer circle are non-continuous. In other words, each of the inner circle and the outer circle is not a full circle, but includes an opening (or equivalently, the ophthalmic liquid delivery ring 300 is not a full ring and includes a break instead). The amount of the opening defines an angle relative to the center of each of the two circles. The angle can vary between one degree and two-hundred seventy degrees.

Such a concentric, non-continuous shape of the ophthalmic liquid delivery ring 300 provides the benefit of adaptively accommodating a range of eye curvatures and sizes by varying the non-continuous opening automatically upon application to the eye. In certain examples, the ophthalmic liquid delivery ring 300 is manufactured larger, and relies upon the accommodation of the curvature to constrict the one or more flow path traces within it to induce therapeutic liquid flow. The positive constriction increases retention of the ophthalmic liquid delivery ring 300 without the need for the ophthalmic liquid delivery ring 300 to extend further back into the orbit of the eye. Therapeutic liquid flow may permeate toward the inner opening and/or the non-continuous opening according to the treatment being for corneal, or conjunctival application by selective placement of one or more outlets and the ratio there between. The non-continuous opening may be varied in size and further be advantageous in locating and preventing interaction with other the ophthalmic liquid delivery ring 300 with specific quadrant locations: glaucoma drainage Ahmed valve, sublacrimal shunt, trabecular shunt, posterior drug delivery device, etc. The non-continuous opening may be of a variety of sizes such as, ten degrees, ninety degrees, one-hundred twenty degrees, and even two-hundred seventy degrees. For the larger openings, the eye contacting surface of the ophthalmic liquid delivery ring 300 may be coarse, treated with a higher stiction material, supported by a tether, supplemented by suture holes, or a combination thereof.

Figure 4:
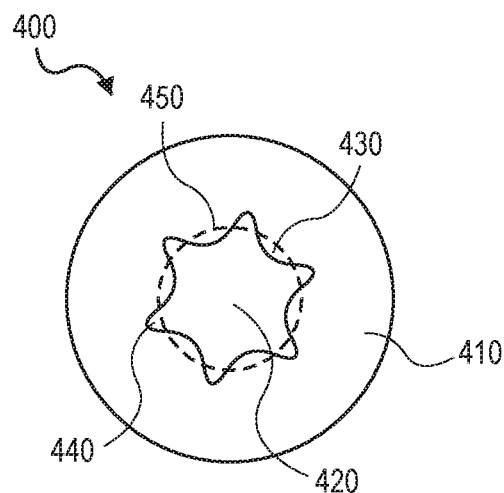
FIG. 4 illustrates a top view of another example ophthalmic liquid delivery ring that includes inner flaps in accordance with an embodiment.

FIG. 4 illustrates a top view of another example ophthalmic liquid delivery ring 400 that includes inner flaps in accordance with an embodiment. The ophthalmic liquid delivery ring 400 is an example of the ophthalmic liquid delivery ring 100 of FIG. 1.

In an example, the ophthalmic liquid delivery ring 400 includes an annular body 410 and an optical zone 420. The optical zone 420 is at the center of the annular body 410 and is hollow. Similarly to the ophthalmic liquid delivery ring 200 of FIG. 2, the ophthalmic liquid delivery ring 400 has an inner parameter and an outer parameter, where the inner perimeter and the optical zone 420 are defined relative to an inner circle (illustrated with a dashed line 450) that has a diameter between eight and twelve millimeters, where the outer perimeter is defined relative to an outer circle that has a diameter between twenty and one hundred millimeters, and where the inner circle 450 and the outer circle are concentric. However, and unlike the ophthalmic liquid delivery ring 200 of FIG. 2, the inner perimeter is not parallel to the inner circle 450. Instead, the inner perimeter generally follows the inner circle 450, while including protrusions 430 and recessions 440 around the inner circle 450. These protrusions 430 and recessions 440 represent flaps (e.g., outer flaps protruding relative to the inner circle 450 and inner flaps receding relative to the inner circle 450). Similar to the ophthalmic liquid delivery ring 300 of FIG. 3, the flaps here provide the benefit of adaptively accommodating a range of eye curvatures and sizes and of allowing improved retention or mounting on the eye. In this example, two opposite points of the inner perimeter are found on opposite protrusions 430, and the shortest distance between the two opposite points is in the range of eight to twelve millimeters. In a specific example, the shortest distance is ten millimeters or about ten millimeters. The two opposite points of the inner perimeter can correspond to two opposite points of the optical zone 430. The largest distance between two opposite points of the inner perimeters are found on opposite recessions 440. The largest distance is in the range of ten to fourteen millimeters. In a specific example, the largest distance is twelve millimeters or about twelve millimeters.

Figure 5:
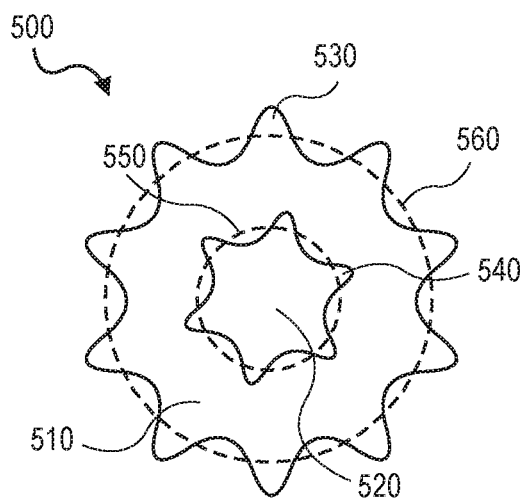
FIG. 5 illustrates a top view of another example ophthalmic liquid delivery ring that includes outer flaps in accordance with an embodiment.

FIG. 5 illustrates a top view of another example ophthalmic liquid delivery ring that includes outer flaps in accordance with an embodiment. The ophthalmic liquid delivery ring 500 is an example of the ophthalmic liquid delivery ring 100 of FIG. 1.

In an example, the ophthalmic liquid delivery ring 500 includes an annular body 510 and an optical zone 520. The optical zone 520 is at the center of the annular body 510 and is hollow. Similarly to the ophthalmic liquid delivery ring 200 of FIG. 2, the ophthalmic liquid delivery ring 500 has an inner parameter and an outer parameter, where the inner perimeter and the optical zone 520 are defined relative to an inner circle (illustrated with a dashed line 550) that has a diameter between eight and twelve millimeters, where the outer perimeter is defined relative to an outer circle (illustrated with a dashed line 560) that has a diameter between twenty and one hundred millimeters, and where the inner circle 450 and the outer circle are concentric. Further, and like the ophthalmic liquid delivery ring 200 of FIG. 2, the inner perimeter of the ophthalmic liquid delivery ring 500 includes flaps 540. In addition, the outer perimeter of the ophthalmic liquid delivery ring 500 includes flaps 530. In particular, and unlike the ophthalmic liquid delivery ring 400 of FIG. 4, the outer perimeter is not parallel to the outer circle 560. Instead, the outer perimeter generally follows the outer circle 560, while including protrusions and recessions around the outer circle 560. These protrusions and recessions represent the flaps 530 (e.g., outer flaps protruding relative to the outer circle 560 and inner flaps receding relative to the outer circle 560). Similar to the ophthalmic liquid delivery ring 400 of FIG. 4, the flaps 530 here provide the benefit of adaptively accommodating a range of eye curvatures and sizes and of allowing improved retention or mounting on the eye.

Figure 6:
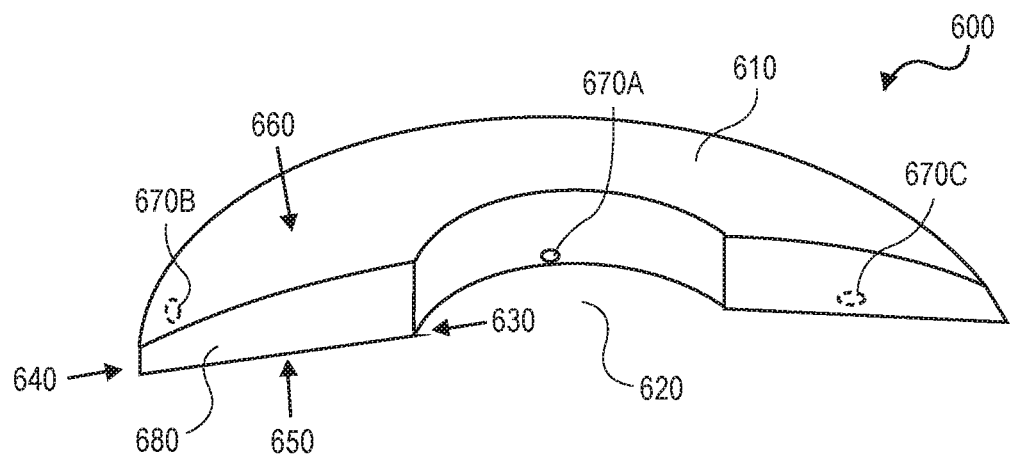
FIG. 6 illustrates a cross sectional view of an example ophthalmic liquid delivery ring in accordance with an embodiment.

FIG. 6 illustrates a cross sectional view of an example ophthalmic liquid delivery ring 600 in accordance with an embodiment. The ophthalmic liquid delivery ring 600 is an example of the ophthalmic liquid delivery ring 100 of FIG. 1.

In an example, the ophthalmic liquid delivery ring 600 includes an annular body 610 and an optical zone 620. The optical zone 620 is at the center of the annular body 610 and is hollow. The annular body 610 is defined by an inner perimeter 630 that surrounds the optical zone 620, an outer perimeter 640 opposite the inner perimeter 630, a bottom surface 650 between the inner perimeter 630 and the outer perimeter 640, and a top surface 660 opposite the bottom surface 650.

In an example, the outer perimeter 640 can be a wall having a certain height (e.g., one to five millimeters). A bottom end of the wall may be connected to the bottom surface 650. A top end of the wall may be connected to the top surface 660. In addition or in the alternative, the outer perimeter 640 can be formed as the junction of the bottom surface 650 and the top surface 660.

In an example, the inner perimeter 630 can be a wall having a certain height (e.g., one to five millimeters). The heights of the inner perimeter 630 and outer perimeter can be the same or can be different. A bottom end of the wall of the inner perimeter 630 may be connected to the bottom surface 650. A top end of this wall may be connected to the top surface 660. In addition or in the alternative, the inner perimeter 630 can be formed as the junction of the bottom surface 650 and the top surface 660.

Each of the bottom surface 650 and the top surface 660 can extend between the inner perimeter 630 and the outer perimeter 660 according to a certain curvature. The curvatures of the bottom surface 650 and the top surface 660 can be the same or substantially the same so that the bottom surface 650 and the top surface 660 are parallel to each other. Alternatively, these curvatures can be different. Generally, at least the curvature of the bottom surface 650 is concave and can be substantially similar to the curvature of the sclera. When worn on an eye, the bottom surface 650 sits on the sclera of the eye. Accordingly, the bottom surface can be configured as a stiction surface, by using a material that has a high static friction and, optionally, by including corrugations or other frictional elements in the bottom surface 650 to increase its friction. In addition, the bottom surface 650 can be connected to a tether (e.g., one shaped like a flap), where the tether includes one or more suture holes. The tether can be generally directed away from the inner perimeter 620 (e.g., the optical zone) and can be on the side of the outer perimeter 620. For instance, and referring back to FIG. 5, the one or more of the flaps 530 can include suture holes.

Furthermore, each of the inner perimeter 630, the outer perimeter 640, the bottom surface 650, and the top surface 660 can have a thickness. The thicknesses can, but need not, be the same. An example thickness is in the range of one to five millimeters. In addition, each of the inner perimeter 630, the outer perimeter 640, the bottom surface 650, and the top surface 660 can be made of a biocompatible material, such as glass, silicone, parylene or any other bio safe flexible material suitable for being worn on the eye and that can be formed into a targeted curvature.

Generally, a space can exist between the bottom surface 650 and the top surface 660. In an example, the space extends to occupy the entire height a portion of the height (e.g., 50%) between the bottom surface 650 and the top surface 660. The space can extend across to be bounded between the inner perimeter 630 and the outer perimeter 640. In this case, the space occupies the entire volume defined by the inner perimeter 630, the outer perimeter 640, the bottom surface 650, and the top surface 660. The volume can be in the range of twenty to five-hundred cubic millimeters. In other illustrations, the space occupies only a portion of the volume defined by the inner perimeter 630, the outer perimeter 640, the bottom surface 650, and the top surface 660. In addition, multiple spaces can be defined in the volume, so as to form multiple pockets within the volume.

A space can be used to define one or more chambers and one or more channels, where a chamber can be a therapeutic liquid storage chamber and/or a pressure chamber, and a channel can be a delivery channel, a flow restrictor channel, and/or a flow channel. For instance, one space can be the therapeutic liquid storage chamber having an output port. A space adjacent thereto can be a pressure chamber. Another space can define a delivery channel connected to the output port. In another illustration, one space can be a therapeutic liquid storage chamber and a pressure chamber separated by a flexible membrane. Of course other implementations are possible for configuring the available volume defined by the inner perimeter 630, the outer perimeter 640, the bottom surface 650, and the top surface 660 to include any or a combination of a therapeutic liquid storage chamber, a pressure chamber, a delivery channel, a flow restrictor channel, and/or a flow channel. Generally, a therapeutic liquid storage chamber can be a space that stores a therapeutic liquid. A pressure chamber can be a space that stores a pressure source that can provide pressure to cause (e.g., push or draw) a flow of a therapeutic liquid from a therapeutic liquid storage chamber. A delivery channel can be a space through which a therapeutic liquid flows and that can be connected to a therapeutic liquid outlet that dispenses the therapeutic liquid flows to the outside of the ophthalmic liquid delivery ring 600. A flow restrictor channel can be a space through which a therapeutic liquid flows, where the space controls the rate of the flow. A flow channel can be a space through which a therapeutic liquid flows. A delivery channel and a flow restrictor channel are examples of a flow channel.

As further illustrated, the ophthalmic liquid delivery ring 600 can include one or more therapeutic liquid outlets (illustrated with element numbers 670A, 670B, and 670C; a therapeutic liquid outlet is referred to herein as an outlet 670). An outlet 670 can be configured to deliver a therapeutic liquid to the outside of the ophthalmic liquid delivery ring 600. Different types of deliveries are possible depending on the type of the outlet 670. For instance, the outlet 670 includes an opening, thereby allowing a delivery through a flow. The outlet 670 can be a membrane made out of a material permeable to the therapeutic liquid, thereby allowing a delivery through permeation. In addition, the outlet 670 can include a one way valve having a flow direction that is outwards from the ophthalmic liquid delivery ring 600. Additionally, the outlet 670 can include a one-way valve having an opposite flow direction or a two-way valve, depending on the need for bringing liquid into the ophthalmic liquid delivery ring 600.

The location of the outlet 670 can also depend on the targeted treatment or use of the ophthalmic liquid delivery ring 600. For instance, for a delivery of the therapeutic liquid into an optical zone of the eye (e.g., the cornea), the outlet 670 can be located in the inner perimeter 630 and, in some instances, close to the bottom surface 650 (as shown with the outlet 670A). For a delivery of the therapeutic liquid onto the sclera (for treating eye dryness), the outlet 670 can be located in the bottom surface 650 (as shown with the outlet 670B). For a delivery of the therapeutic liquid into an outer side of the eye (for treating allergies), the outlet 670 can be located in the outer perimeter 640 and, in some instances, close to the bottom surface 650 (as shown with the outlet 670C).

One or more types of therapeutic liquid can be stored within the volume of the ophthalmic liquid delivery ring 600. This volume can include a single therapeutic liquid storage chamber or a plurality of therapeutic liquid storage chambers. A therapeutic liquid storage chamber can store one or more therapeutic liquids as one or more mixes or separately. The types of therapeutic liquid include liquid drugs. The types also include a fluid solution that includes an organism (e.g., bacteria, eukaryotic cell, engineered cell), components of a synthesis pathway, and/or catalysts/enzyme capable of inducing a therapeutic effect. For instance, an organism could synthesize a therapeutic molecule or drug and receive necessary nutrients from a tear of an eye or a nutrient chamber within the ophthalmic liquid delivery ring 600. Similarly, components of a synthesis pathway could utilize compounds from the tear and/or from a chamber to synthesize a therapeutic molecule. A catalyst/enzyme could also be used to modify compounds into therapeutics. A pro-drug could be housed in the ophthalmic liquid delivery ring 600 and undergo catalyst-limited reaction to produce a drug. If a semipermeable membrane selective for the drug but not the pro-drug is utilized, zero-order reaction kinetics can be achieved. In a similar manner, harmful molecules in the tear film could be neutralized by the housed organisms, chemicals, or catalyst/enzymes.

Figure 7:
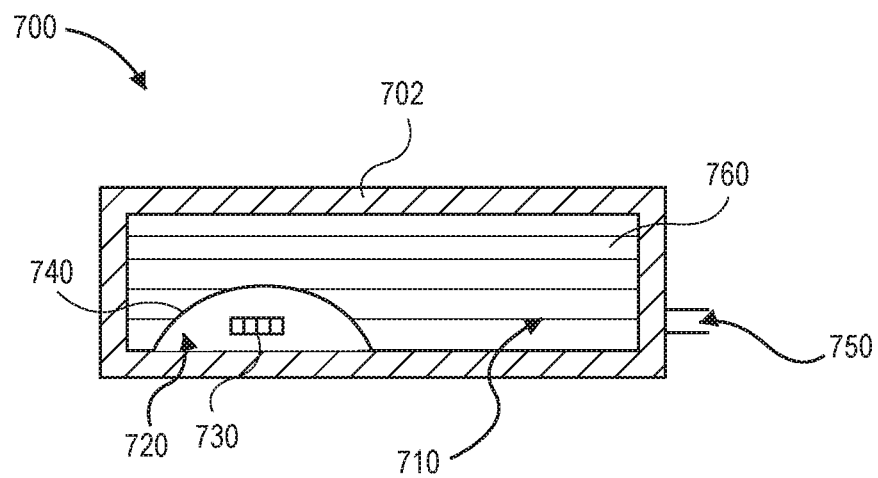
FIG. 7 illustrates an arrangement of an ophthalmic liquid delivery ring that includes a pressure chamber in accordance with an embodiment.

FIG. 7 illustrates an arrangement of an ophthalmic liquid delivery ring 700 that includes a pressure chamber 720 in accordance with an embodiment. The ophthalmic liquid delivery ring 700 is an example of the ophthalmic liquid delivery ring 100 of FIG. 1. The shown arrangement illustrates a cross section of a portion of the ophthalmic liquid delivery ring 700.

In particular, the ophthalmic liquid delivery ring 700 an annular body 702, formed by a material of a particular thickness. The annular body 702 contains a volume that is divided between the pressure chamber 720 and a therapeutic liquid storage chamber 710. A flexible membrane 740 separates the pressure chamber 720 and the therapeutic liquid storage chamber 710. This membrane can be made of flexible material, such as silicone or parylene having a particular thickness (e.g., in the range of 0.1 to two millimeters). The pressure chamber 720 houses a pressure source 730. In comparison, the therapeutic liquid storage chamber 710 stores a therapeutic liquid.

In addition, the ophthalmic liquid delivery ring 700 includes a therapeutic liquid outlet 750 that is coupled to the therapeutic liquid storage chamber 710. In operation, pressure from the pressure source 730 inside the pressure chamber 720 actuates the flexible membrane 740, causing a push or draw of a portion of the therapeutic liquid from the therapeutic liquid storage chamber 710, where this portion flows to the therapeutic liquid outlet 750 for delivery to the outside of the ophthalmic liquid delivery ring 700.

Figure 8:
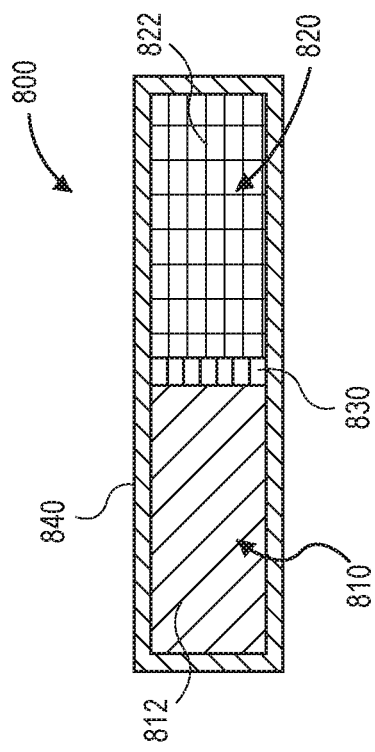
FIG. 8 illustrates an example pressure source for a pressure chamber of an ophthalmic liquid delivery ring in accordance with an embodiment.
Figure 8:
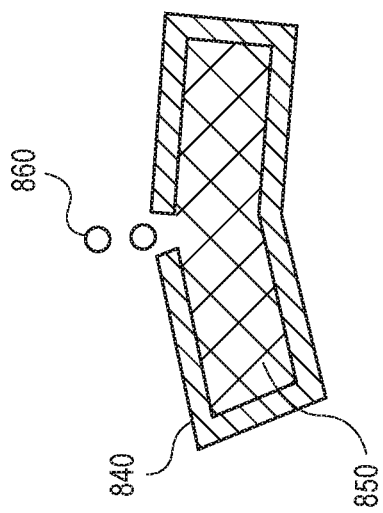

FIG. 8 illustrates an example pressure source for a pressure chamber of an ophthalmic liquid delivery ring in accordance with an embodiment. More specifically, FIG. 8 shows a cross section of the pressure source. The pressure source is an example of the pressure source 730 of FIG. 7.

As illustrated, the pressure source includes a chamber 800 defined by an external membrane 840. The chamber 800 can be of any shape and size, such as a rectangular cuboid, and defines a volume. The external membrane 840 can be a bio safe membrane made with a frangible material that breaks based on mechanical pressure applied from an external source onto the pressure source (or, equivalently, the chamber 800), that breaks based on mechanical pressure applied internally from the chamber 800 (e.g., based on gas pressure buildup), or that can be permeable to the gas molecules and need not break upon an external or internal pressure application. For instance, the external membrane 840 can be made out of a thin glass (e.g., with a thickness less than one millimeter) or a thin parylene material (e.g., with a thickness less than one micrometer).

In addition, the chamber 800 includes one or more internal membranes 830 that divide the volume of the chamber 800 into multiple sub-volumes. Each of such sub-volumes can define a chemical storage chamber for storing a bio safe chemical. An internal membranes 830 acts as a barrier or a seal between at least two of such chemical storage chambers to avoid the stored chemicals from mixing with each other. The internal membrane 830 can be a bio safe membrane that breaks based on mechanical pressure applied from an external source onto the pressure source (or, equivalently, the chamber 800). For instance, the internal membrane 810 can be made out of a thin glass (e.g., with a thickness less than one millimeter).

As illustrated, the chamber 800 is divided into two chemical storage chambers 810 and 820 that are separated by an internal membrane 830. The first chemical storage chamber 810 stores a first bio safe chemical 812. Similarly, the second chemical storage chamber 820 stores a second bio safe chemical 822. When these two chemicals 812 and 822 are separated from each other, no chemical decomposition occurs. For instance, the first bio safe chemical 812 can be an acetic acid and the second bio safe chemical 822 can be baking soda ($NaHCO_3$). In another illustration, the first bio safe chemical 812 can be peroxide and the second bio safe chemical 822 can be platinum.

As further illustrated in FIG. 8, upon a mechanical pressure applied to the chamber 800, the internal membrane 830 is broken, allowing the first bio safe chemical 812 and the second bio safe chemical 822 to mix, thereby creating a mix 850 of the two chemicals 812 and 822. This mix results in a release of gas molecules 860. The gas molecules 860 can be released out of the chamber 800 (e.g., based on the outer membrane 840 being also broken by the same mechanical pressure, a different external pressure, or an internal pressure buildup, or based on permeation).

Figure 9:
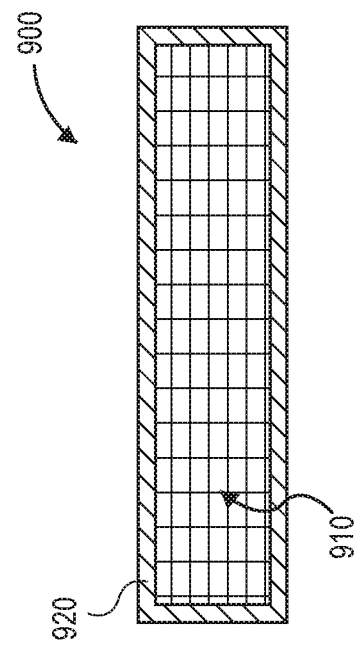
FIG. 9 illustrates another example pressure source for a pressure chamber of an ophthalmic liquid delivery ring in accordance with an embodiment.
Figure 9:
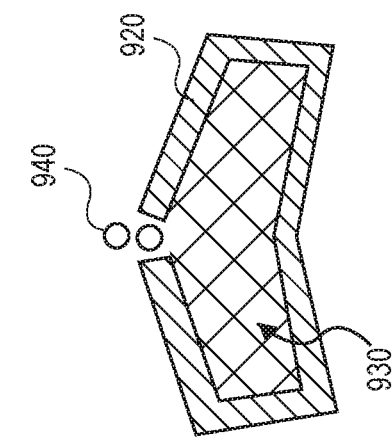

FIG. 9 illustrates another example pressure source for a pressure chamber of an ophthalmic liquid delivery ring in accordance with an embodiment. More specifically, FIG. 9 shows a cross section of the pressure source. The pressure source is an example of the pressure source 730 of FIG. 7.

As illustrated, the pressure source includes a chamber 900 defined by an external membrane 920. The chamber 920 can be of any shape and size, such as a rectangular cuboid, and defines a volume. The external membrane 920 can be a bio safe membrane made with a frangible material that breaks based on mechanical pressure applied internally from the chamber 800 (e.g., based on gas pressure buildup), or that can be permeable to the gas molecules and need not break upon an external or internal pressure application. For instance, the external membrane 920 can be made out of a thin glass (e.g., with a thickness less than one millimeter) or a thin parylene material (e.g., with a thickness less than one micrometer).

In addition, the volume of the chamber 900 is occupied entirely or partially by a bio safe phase changing material 910. This material 910 can be in a first state (e.g., solid or liquid) at a first temperature and change to a second state (e.g., gas) at a second temperature. Accordingly, upon a change from the first temperature to a temperature that exceeds the second temperature (or, depending on the material, change to a temperature that is below the second temperature), the bio safe phase changing material 910 changes to the second state (shown in the figure as element 930), where gas molecules 940 are released in this second state. The gas molecules 940 can be released out of the chamber 900 (e.g., based on the outer membrane 920 being broken by an external pressure application or an internal pressure buildup, or based on permeation).

The bio safe phase changing material 910 can be material that is bio safe and that expands upon phase change within the desired temperature range of an ophthalmic liquid delivery ring that is a suitable phase change material. In an example, the phase change occurs within a temperature range in the normal temperature range encountered during a daily life of the patient (e.g., 50° F. and 160° F., more specifically between 70° F. and 120° F.). For instance, the bio safe phase changing material 910 can be perfluorocarbon (PFC). In another example, the phase change occurs from a built in heating element in the chamber 900 or in a pressure chamber that contains the chamber 900. By using different phase change materials, the rate of fluid delivery can be tailored to meet specific needs.

Figure 10:
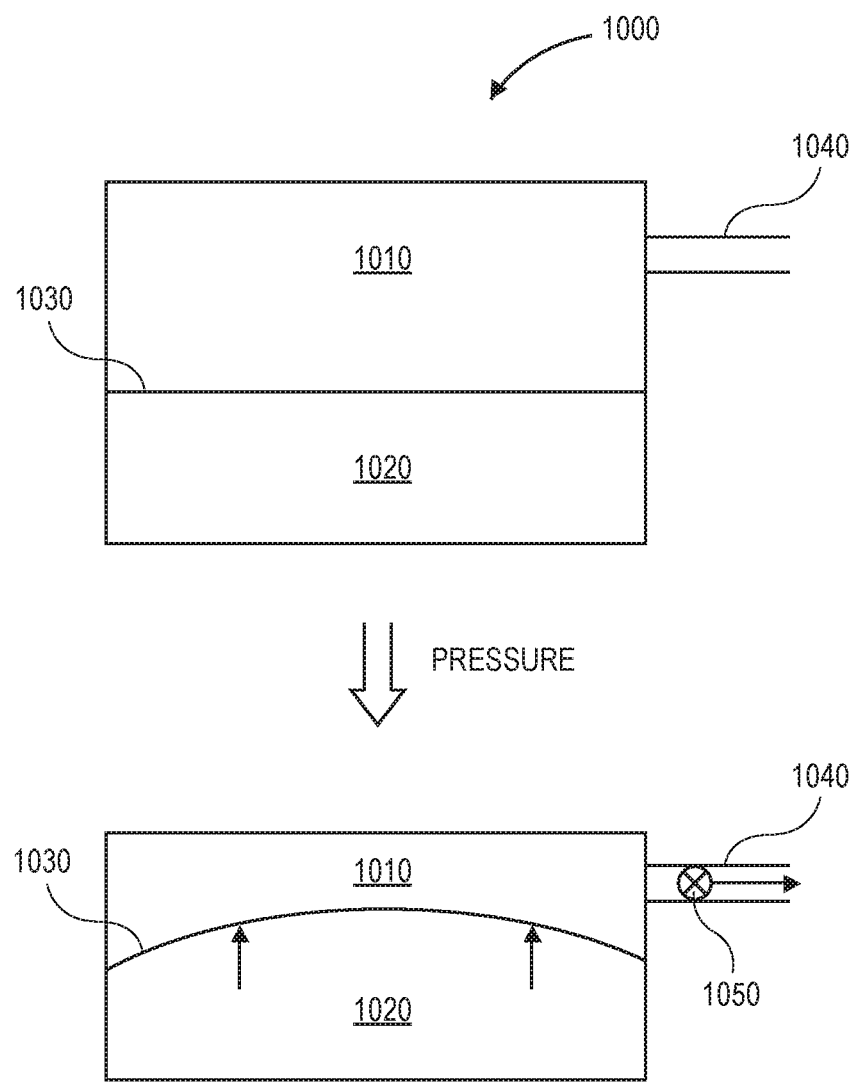
FIG. 10 illustrates a pressure-based actuation of a membrane in a pressure source of an ophthalmic liquid delivery ring in accordance with an embodiment.

FIG. 10 illustrates a pressure-based actuation of a membrane in a pressure chamber of an ophthalmic liquid delivery ring 1000 in accordance with an embodiment. The ophthalmic liquid delivery ring 1000 is an example of the ophthalmic liquid delivery ring 100 of FIG. 1. The pressure-based actuation can occur according to release of gas molecules based on chemical decomposition as illustrated in connection with FIG. 8 or based on a phase change as illustrated in connection with FIG. 9.

In an example, the ophthalmic liquid delivery ring 1000 includes a therapeutic liquid storage chamber 1010 storing a therapeutic liquid, a pressure chamber 1020 containing a pressure source, a flexible membrane 1030 (e.g., a flexible diaphragm), and a therapeutic liquid outlet 1040 coupled with the therapeutic liquid storage chamber 1010. Upon a release of gas molecules, a pressure is applied to the flexible membrane internally from the pressure chamber 1020 (shown at the bottom of FIG. 2 with two arrows directed upwards). Upon sufficient pressure buildup, the flexible membrane 1030 bows into the therapeutic liquid storage chamber 1010, increasing pressure within the therapeutic liquid storage chamber 1010, causing a flow of a portion 1050 of the therapeutic liquid from the therapeutic liquid storage chamber 1010 to the therapeutic liquid outlet 1040.

Figure 11:
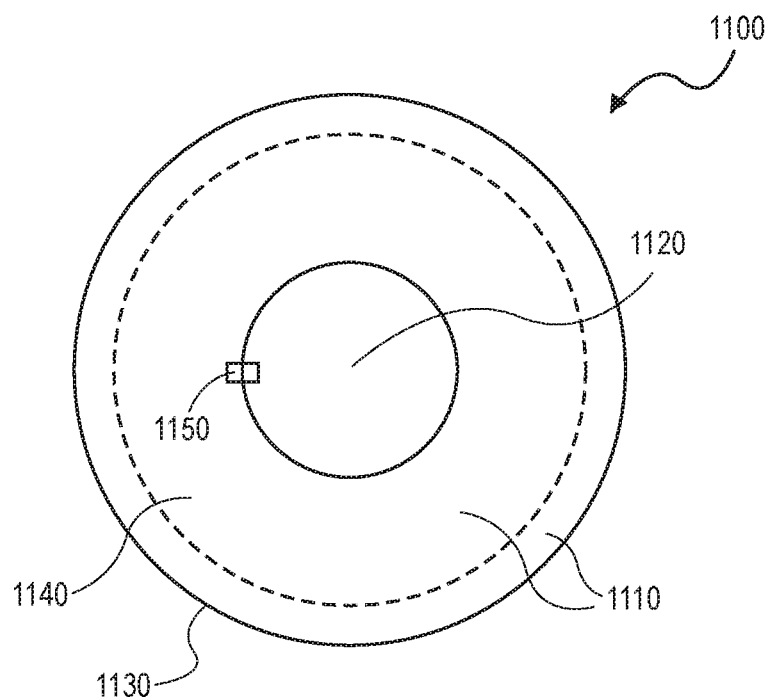
FIG. 11 illustrates a top view of an example ophthalmic liquid delivery ring that includes a pressure chamber in accordance with an embodiment.

FIG. 11 illustrates a top view of an example ophthalmic liquid delivery ring 11000 that includes a pressure chamber in accordance with an embodiment. The ophthalmic liquid delivery ring 1100 is an example of the ophthalmic liquid delivery ring 100 of FIG. 1.

In an example, the ophthalmic liquid delivery ring 1100 includes an annular body 1110 and an optical zone 1120. The optical zone 1120 is at the center of the annular body 1110. The annular body 1110 contains a pressure chamber 1130, a therapeutic liquid storage chamber 1140, and a therapeutic liquid outlet 1150.

The pressure chamber 1130 can occupy a portion of the volume within the ophthalmic liquid delivery ring 1100, whereas the therapeutic liquid storage chamber 1140 occupies the remaining portion of the volume. In particular, the pressure chamber 1130 can be contained near the outer perimeter of the annular body 1102 and have an annular volume. The annular volume can be located underneath the therapeutic liquid storage chamber 1140, as illustrated with the dashed line in FIG. 11. However, the annular volume can instead be located on top of the therapeutic liquid storage chamber 1140.

In addition, the therapeutic liquid storage chamber 1140 can store a therapeutic liquid and include a port. The therapeutic liquid outlet 1150 can include an input port and an output port. The input port of the therapeutic liquid outlet 1150 can be connected with the port of the therapeutic liquid storage chamber 1140. The output port of the therapeutic liquid outlet 1150 can be directed outward from the ophthalmic liquid delivery ring 1100 and can include a one way valve, such that the therapeutic liquid can flow through the output port to the outside of the ophthalmic liquid delivery ring 1100.

Figure 12:
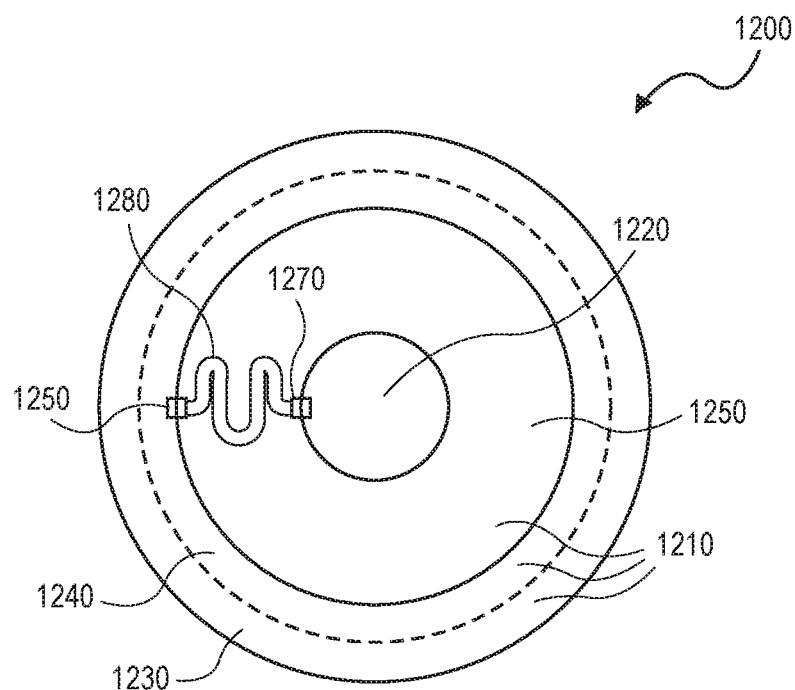
FIG. 12 illustrates a top view of another example ophthalmic liquid delivery ring that includes a pressure chamber in accordance with an embodiment.

FIG. 12 illustrates a top view of another example ophthalmic liquid delivery ring 1200 that includes a pressure chamber in accordance with an embodiment. The ophthalmic liquid delivery ring 1200 is an example of the ophthalmic liquid delivery ring 100 of FIG. 1.

In an example, the ophthalmic liquid delivery ring 1200 includes an annular body 1210 and an optical zone 1220. The optical zone 1220 is at the center of the annular body 1210. The annular body 1210 contains a pressure chamber 1230, a therapeutic liquid storage chamber 1240, a therapeutic liquid outlet 1270, and a delivery channel 1280.

The pressure chamber 1230 can occupy a first portion of the volume within the ophthalmic liquid delivery ring 1200, whereas the therapeutic liquid storage chamber 1240 occupies a second portion (but not the remaining portion) of the volume. In particular, the pressure chamber 1230 can be contained near the outer perimeter of the annular body 1210 and have an annular volume that is located underneath (or on top of) the therapeutic liquid storage chamber 1140.

In addition, the therapeutic liquid storage chamber 1240 can store a therapeutic liquid and include a port 1250. The therapeutic liquid outlet 1270 is coupled with the therapeutic liquid storage chamber 1240 through the delivery channel 1280. In particular, each of the therapeutic liquid outlet 1270 and the delivery channel 1280 can include an input port and an output port. The input port of the therapeutic liquid outlet 1270 can be connected with the output port of delivery channel 1280. In turn, the input port of the delivery channel 1280 can be connected to the port 1250 of the therapeutic liquid storage chamber 1240. The output port of the therapeutic liquid outlet 1270 can be directed outward from the ophthalmic liquid delivery ring 1200, such that the therapeutic liquid can flow through the output port to the outside of the ophthalmic liquid delivery ring 1200. One, some, or all of the input and output ports and the port 1250 can include a one way valve. In addition, the delivery channel 1280 can include a flow restrictor.

The flow restrictor can be a suitable metering valve/flow regulator/pressure regulator. In an example, one or more metering valves/flow regulators/pressure regulators can be coupled to achieve the desired flow rate of therapeutic liquid into the eye. In an example, the flow restrictor can be a high-fluidic-resistance channel. A high-fluidic-resistance channel can be any channel with a high resistance including channels with small apertures or channels with solid material that increases the resistance of the fluid passing through. In another example, the flow restrictor can include one or more dissolvable barriers (e.g., dissolvable beads) placed within the delivery channel 1280 and that dissolve over time at a targeted rate based on contact with the therapeutic fluid, thereby changing the aperture of the delivery channel 1280 over time.

Figure 13:
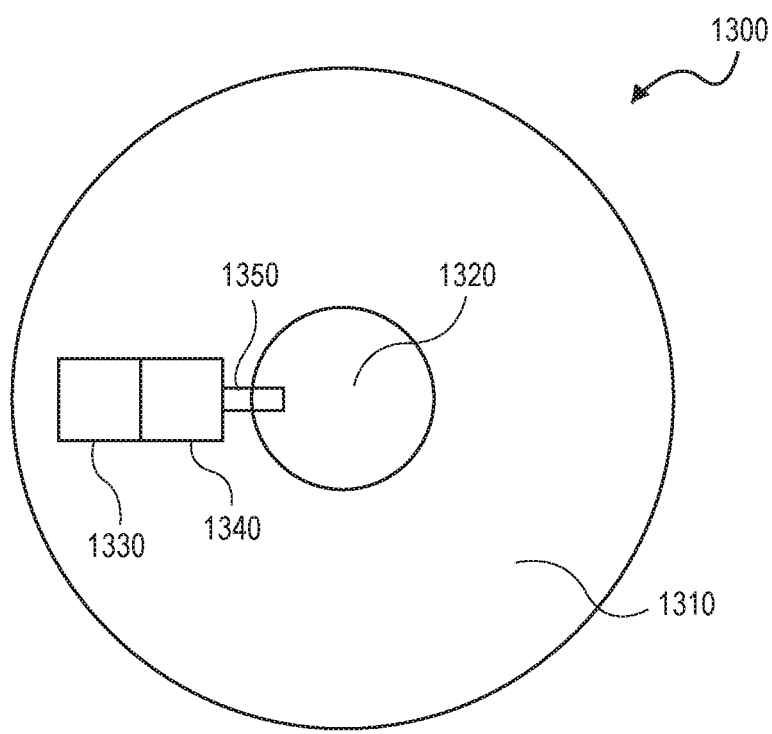
FIG. 13 illustrates a top view of yet another example ophthalmic liquid delivery ring that includes a pressure chamber in accordance with an embodiment.

FIG. 13 illustrates a top view of yet another example ophthalmic liquid delivery ring 1300 that includes a pressure chamber in accordance with an embodiment. The ophthalmic liquid delivery ring 1300 is an example of the ophthalmic liquid delivery ring 100 of FIG. 1.

In an example, the ophthalmic liquid delivery ring 1300 includes an annular body 1310 and an optical zone 1320. The optical zone 1320 is at the center of the annular body 1310. The annular body 1310 contains a pressure chamber 1330, a therapeutic liquid storage chamber 1340, and a therapeutic liquid outlet 1350.

The pressure chamber 1330 can occupy a first portion of the volume within the ophthalmic liquid delivery ring 1300, whereas the therapeutic liquid storage chamber 1340 occupies a second portion of the volume. In particular, the pressure chamber 1330 need not have an annular volume. Instead, the pressure chamber 1330 can have any shape and can be defined as a pocket or some other space within the annular body 1310. Similarly, the therapeutic liquid storage chamber 1340 can have any shape and can be defined as a pocket or some other space within the annular body 1310. Typically, the pressure chamber 1330 and the therapeutic liquid storage chamber 1340 have a common flexible membrane, such as a flexible diaphragm in between. The volumes of the pressure chamber 1330 and the therapeutic liquid storage chamber 1340 can, but need not, be the same.

In addition, the therapeutic liquid storage chamber 1340 can store a therapeutic liquid and include a port. The therapeutic liquid outlet 1350 can include an input port and an output port. The input port of the therapeutic liquid outlet 1350 can be connected with the port of the therapeutic liquid storage chamber 1340. The output port of the therapeutic liquid outlet 1350 can be directed outward from the ophthalmic liquid delivery ring 1300 and can include a one way valve, such that the therapeutic liquid can flow through the output port to the outside of the ophthalmic liquid delivery ring 1300.

Figure 14:
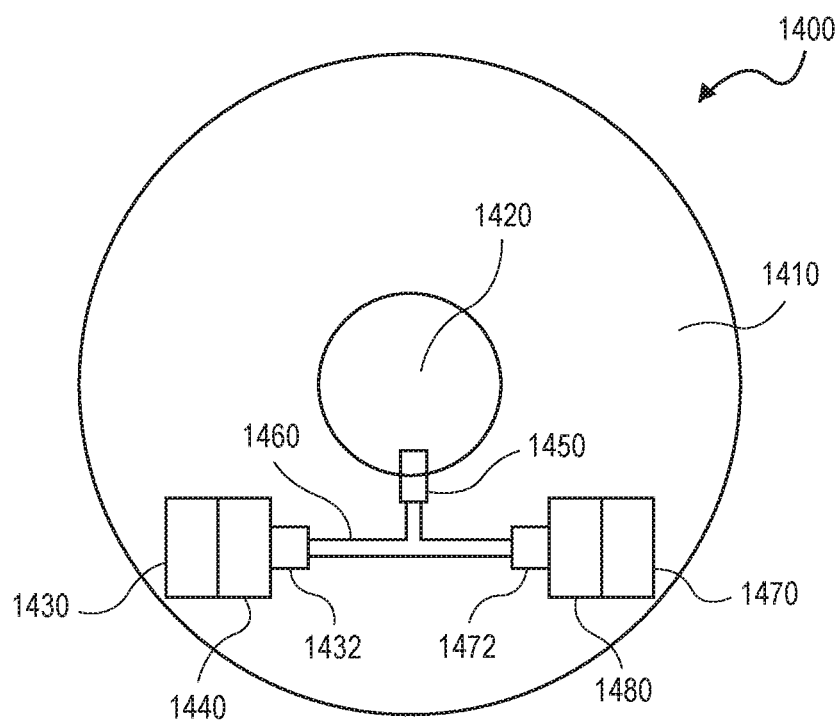
FIG. 14 illustrates a top view of a further example ophthalmic liquid delivery ring that includes a pressure chamber in accordance with an embodiment.

FIG. 14 illustrates a top view of a further example ophthalmic liquid delivery ring 1400 that includes a pressure chamber in accordance with an embodiment. The ophthalmic liquid delivery ring 1400 is an example of the ophthalmic liquid delivery ring 100 of FIG. 1. In addition, the ophthalmic liquid delivery ring 1400 is similar to the ophthalmic liquid delivery ring 1300 of FIG. 13 except that the ophthalmic liquid delivery ring 1400 includes a plurality of pressure chambers and a plurality of therapeutic liquid storage chambers.

In an example, the ophthalmic liquid delivery ring 1400 includes an annular body 1410 and an optical zone 1420. The optical zone 1420 is at the center of the annular body 1410. The annular body 1410 contains a first pressure chamber 1430, a first therapeutic liquid storage chamber 1440, a second pressure chamber 1470, a second therapeutic liquid storage chamber 1480, a therapeutic liquid outlet 1450, and a delivery channel 1460.

The first pressure chamber 1430 can occupy a first portion of the volume within the ophthalmic liquid delivery ring 1400, whereas the first therapeutic liquid storage chamber 1440 occupies a second portion of the volume. In particular, the first pressure chamber 1430 need not have an annular volume. Instead, the first pressure chamber 1430 can have any shape and can be defined as a pocket or some other space within the annular body 1410. Similarly, the first therapeutic liquid storage chamber 1440 can have any shape and can be defined as a pocket or some other space within the annular body 1410. Typically, the first pressure chamber 1430 and the first therapeutic liquid storage chamber 1440 have a common flexible membrane, such as a flexible diaphragm in between. The volumes of the first pressure chamber 1430 and first therapeutic liquid storage chamber 1440 can, but need not, be the same. The first therapeutic liquid storage chamber 1440 can also include a port 1432.

The second pressure chamber 1470 and the second therapeutic liquid storage chamber 1440 have a similar configuration and the similarities are not repeated herein in the interest of brevity. Generally, the volumes of second pressure chamber 1470 and the second therapeutic liquid storage chamber 1480 can, but need not, be the same as the volumes of the first pressure chamber 1430 and first therapeutic liquid storage chamber 1440. In addition, the second therapeutic liquid storage chamber 1480 can store the same type of therapeutic liquid as the first therapeutic liquid storage chamber 1440, a different type of therapeutic liquid as the first therapeutic liquid storage chamber 1440, or other liquids (e.g., non therapeutic that can be mixed with the first therapeutic liquid; alternatively, both storage chambers can store the same or different types of liquids that, when mixed, result in a therapeutic liquid). Similarly, the second therapeutic pressure chamber 1470 can store the same type of pressure source (e.g., chemical decomposition or phase changing based material) as the first pressure chamber 1430 or can store a different type of pressure source as the first pressure chamber 1430.

In addition, the therapeutic liquid outlet 1450 is coupled with each of the first therapeutic liquid storage chamber 1440 and the second therapeutic liquid storage chamber 1480 via the delivery channel 1460. In particular, the delivery channel 1460 connects (e.g., via ports, one way valves, flow restrictors, etc. as discussed herein above in connection with FIG. 12) the port 1432 of the first therapeutic liquid storage chamber 1440 with the therapeutic liquid outlet 1450. Similarly, the delivery channel 1460 connects a port 1472 of the second therapeutic liquid storage chamber 1480 with the therapeutic liquid outlet 1450.

The first and second pressure chambers 1430 and 1440 can be activated at the same time in parallel, thereby allowing first therapeutic liquid to flow from the first therapeutic liquid storage chamber 1440 and second therapeutic liquid to flow from the second therapeutic liquid storage chamber 1480 at the same time, mix in the delivery channel 1460, and be delivered as a mix through the therapeutic liquid outlet 1450. Alternatively, the first and second pressure chambers 1430 and 1440 can be activated at different times, thereby allowing the first therapeutic liquid to flow into the delivery channel 1460 and be delivered through the therapeutic liquid outlet 1450 at a different time from the flow and delivery of the second therapeutic liquid.

Figure 15:
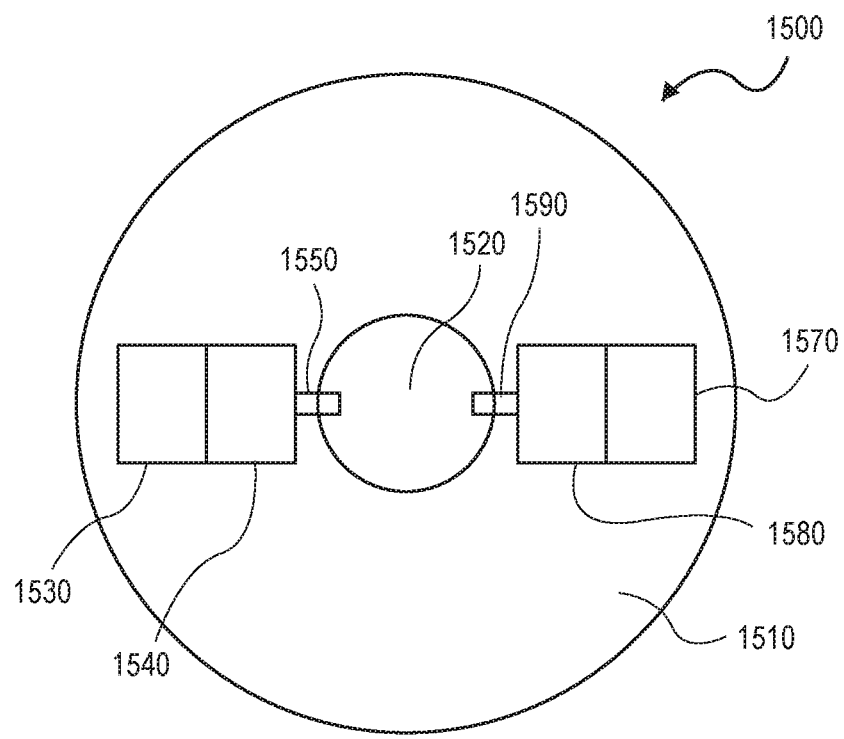
FIG. 15 illustrates a top view of another example ophthalmic liquid delivery ring that includes a pressure chamber in accordance with an embodiment.

FIG. 15 illustrates a top view of another example ophthalmic liquid delivery ring 1500 that includes a pressure chamber in accordance with an embodiment. The ophthalmic liquid delivery ring 1500 is an example of the ophthalmic liquid delivery ring 100 of FIG. 1. In addition, the ophthalmic liquid delivery ring 1500 is similar to the ophthalmic liquid delivery ring 1400 of FIG. 14 by including a plurality of pressure chambers and a plurality of therapeutic liquid storage chambers. However, a difference over the ophthalmic liquid delivery ring 1400 of FIG. 14 is that multiple therapeutic delivery outlets are used in the ophthalmic liquid delivery ring. Similarities between the two rings are not repeated herein in the interest of brevity.

In an example, the ophthalmic liquid delivery ring 1500 includes an annular body 1510 and an optical zone 1520. The optical zone 1520 is at the center of the annular body 1510. The annular body 1510 contains a first pressure chamber 1530, a first therapeutic liquid storage chamber 1540, and a first therapeutic liquid outlet 1550 coupled with (e.g., directly connected with) the first therapeutic liquid storage chamber 1540. The annular body 1510 also contains a second pressure chamber 1570, a second therapeutic liquid storage chamber 1580, and a second therapeutic liquid outlet 1590 coupled with (e.g., directly connected with) the second therapeutic liquid storage chamber 1580.

Figure 16:
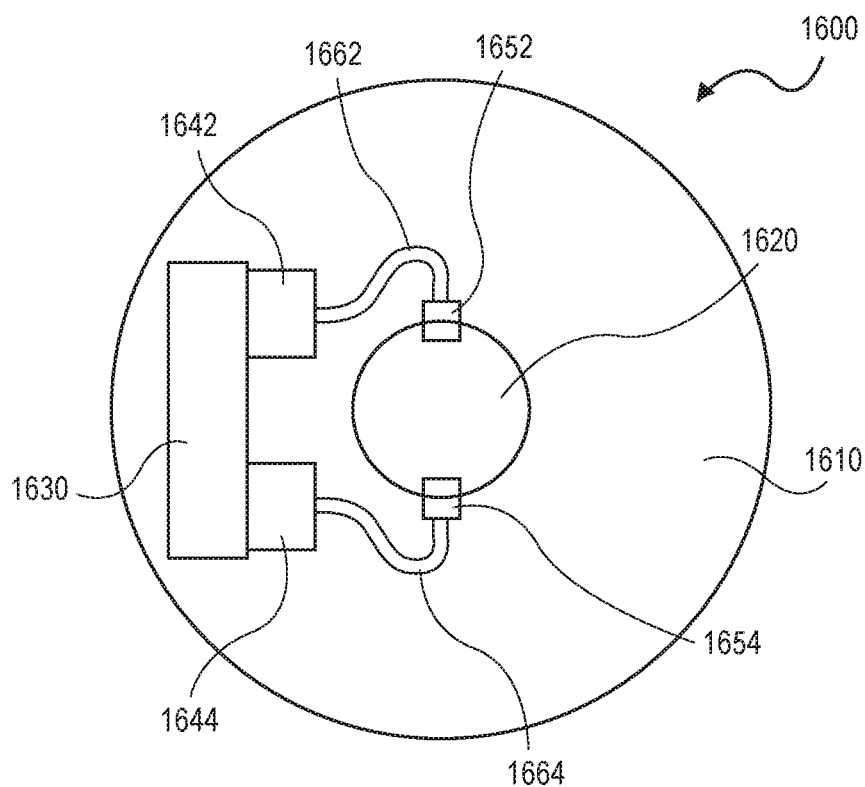
FIG. 16 illustrates a top view of yet another example ophthalmic liquid delivery ring that includes a pressure chamber in accordance with an embodiment.

FIG. 16 illustrates a top view of yet another example ophthalmic liquid delivery ring 1600 that includes a pressure chamber in accordance with an embodiment. The ophthalmic liquid delivery ring 1600 is an example of the ophthalmic liquid delivery ring 100 of FIG. 1. Generally, the ophthalmic liquid delivery ring 1600 include a single pressure chamber 1630 that actuates a plurality of therapeutic liquid storage reservoirs, each of which is coupled with one of a plurality of therapeutic liquid outlets.

In an example, the ophthalmic liquid delivery ring 1600 includes an annular body 1610 and an optical zone 1620. The optical zone 1620 is at the center of the annular body 1610. The annular body 1610 contains the pressure chamber 1630, a first therapeutic liquid storage chamber 1642, a second therapeutic liquid storage chamber 1644, a first therapeutic liquid outlet 1652, a second therapeutic liquid outlet 1654, a first delivery channel 1662, and a second delivery channel 1664.

The pressure chamber 1630 can occupy a first portion of the volume within the ophthalmic liquid delivery ring 1600, whereas the first therapeutic liquid storage chamber 1642 and the second therapeutic liquid storage chamber 1644 occupy a second portion and third portion, respectively, of the volume. In particular, the pressure chamber 1630 need not have an annular volume. Instead, the pressure chamber 1630 can have any shape and can be defined as a pocket or some other space within the annular body 1610. Similarly, each of the first therapeutic liquid storage chamber 1642 and the second therapeutic liquid storage chamber 1644 can have any shape and can be defined as a pocket or some other space within the annular body 1610. Typically, the pressure chamber 1630 and the first therapeutic liquid storage chamber 1642 have a first common flexible membrane, such as a flexible diaphragm in between. Similarly, the pressure chamber 1630 and the second therapeutic liquid storage chamber 1644 have a second common flexible membrane, such as a flexible diaphragm in between. The volumes of the pressure chamber 1630, first therapeutic liquid storage chamber 1642, and second therapeutic liquid storage chamber 1644 can, but need not, be the same. In addition, the second therapeutic liquid storage chamber 1644 can store the same type of therapeutic liquid as the first therapeutic liquid storage chamber 1642 or can store a different type of therapeutic liquid as the first therapeutic liquid storage chamber 1642.

In addition, the first therapeutic liquid outlet 1652 is coupled with the first therapeutic liquid storage chamber 1642. In particular, the first delivery channel 1662 connects (e.g., via ports, one way valves, flow restrictors, etc. as discussed herein above in connection with FIG. 12) the port of the first therapeutic liquid storage chamber 1642 with the first therapeutic liquid outlet 1652. Similarly, the second delivery channel 1664 connects a port of the second therapeutic liquid storage chamber 1644 with the second therapeutic liquid outlet 1654.

Activating the pressure chamber 1630 causes first therapeutic liquid to flow from the first therapeutic liquid storage chamber 1642 and second therapeutic liquid to flow from the second therapeutic liquid storage chamber 1642 at the same time to the respective delivery channel and delivered through the respective therapeutic liquid outlet.

Figure 17:
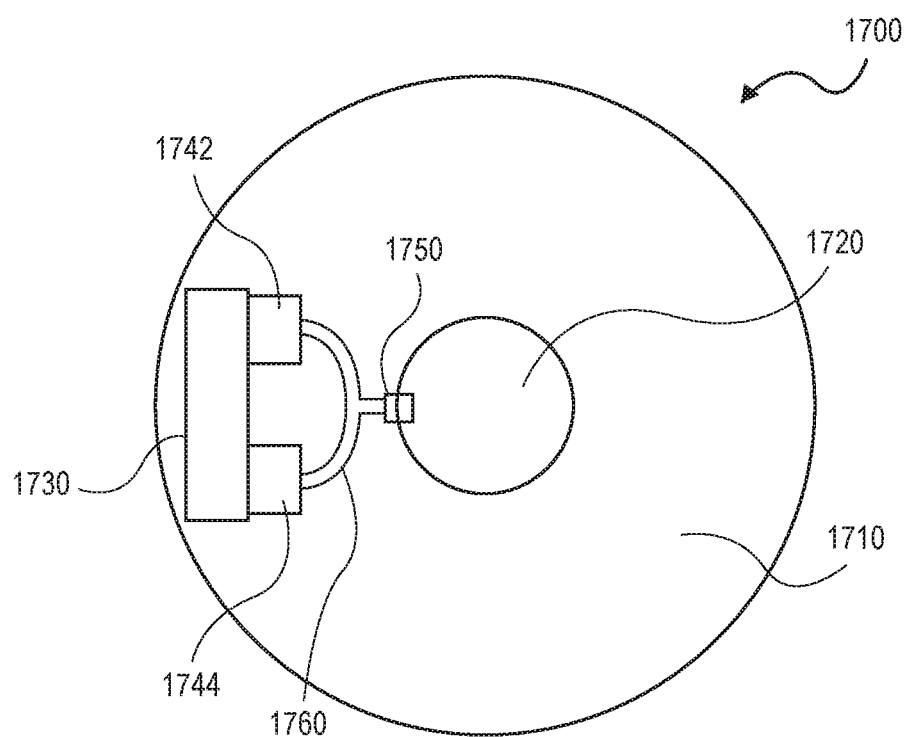
FIG. 17 illustrates a top view of a further example ophthalmic liquid delivery ring that includes a pressure chamber in accordance with an embodiment.

FIG. 17 illustrates a top view of a further example ophthalmic liquid delivery ring 1700 that includes a pressure chamber in accordance with an embodiment. The ophthalmic liquid delivery ring 1700 is an example of the ophthalmic liquid delivery ring 100 of FIG. 1. In addition, the ophthalmic liquid delivery ring 1700 is similar to the ophthalmic liquid delivery ring 1400 of FIG. 14 by including a plurality of therapeutic liquid storage chambers, a delivery channel 1760, and a therapeutic liquid outlet 1750. However, a difference over the ophthalmic liquid delivery ring 1400 of FIG. 14 is that a single pressure chamber 1730 is used, similarly to the ophthalmic liquid delivery ring 1600 of FIG. 16. Similarities between the two rings are not repeated herein in the interest of brevity.

In an example, the ophthalmic liquid delivery ring 1700 includes an annular body 1710 and an optical zone 1720. The optical zone 1720 is at the center of the annular body 1710. The annular body 1710 contains the pressure chamber 1730, a first therapeutic liquid storage chamber 1742, a second pressure chamber 1744, the delivery channel 1760, and the therapeutic liquid outlet 1750. This outlet 1750 is coupled with each of the first therapeutic liquid storage chamber 1742, and second pressure chamber 1744 via the delivery channel 1760.

Figure 18:
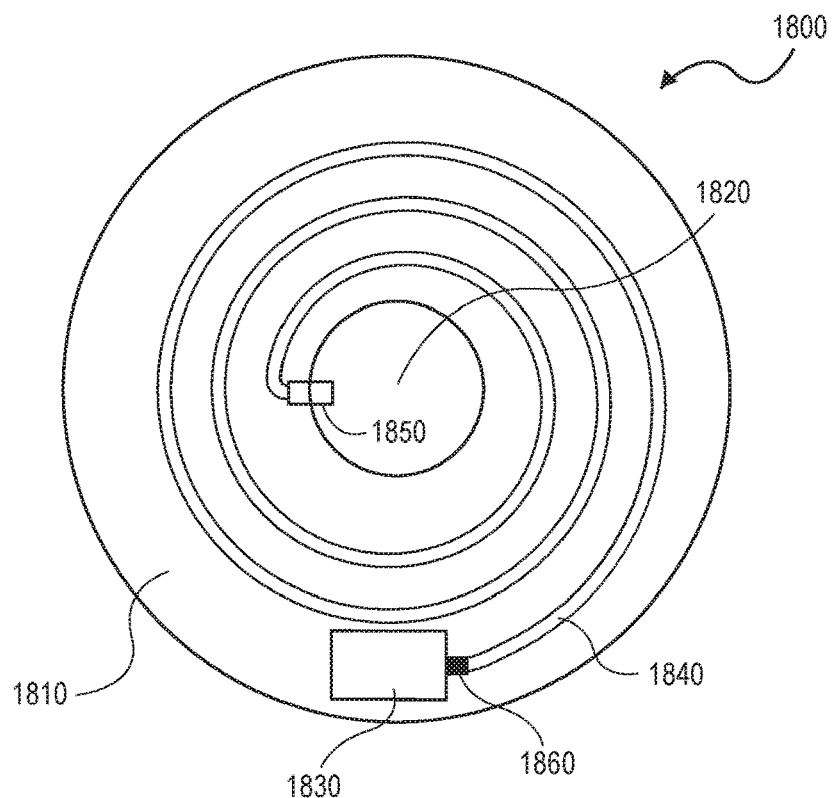
FIG. 18 illustrates a top view of an example ophthalmic liquid delivery ring that includes delivery channel in accordance with an embodiment.

FIG. 18 illustrates a top view of an example ophthalmic liquid delivery ring 1800 that includes delivery channel in accordance with an embodiment. The ophthalmic liquid delivery ring 1800 is an example of the ophthalmic liquid delivery ring 100 of FIG. 1.

In an example, the ophthalmic liquid delivery ring 1800 includes an annular body 1810 and an optical zone 1820. The optical zone 1820 is at the center of the annular body 1810. The annular body 1810 contains a pressure chamber 1830, a therapeutic liquid delivery channel 1840, and a therapeutic liquid outlet 1850. The therapeutic liquid delivery channel 1840 is an example of a delivery channel defined within the annular body 1810. However, the therapeutic liquid delivery channel 1840 in the example of FIG. 18 also stores therapeutic liquid and interfaces with the pressure chamber 1830, thereby acting also like a therapeutic liquid storage chamber. In other words, the therapeutic liquid delivery channel 1840 is a hybrid of a therapeutic liquid storage chamber and a delivery channel.

The pressure chamber 1830 can occupy a first portion of the volume within the ophthalmic liquid delivery ring 1800, whereas the therapeutic liquid delivery channel 1840 occupies a second portion (but not the remaining portion) of the volume. In addition, the therapeutic liquid delivery channel 1840 can store a therapeutic liquid and include an input port and an output port. The therapeutic liquid outlet 1850 can also include an input port and an output port. The input port of the therapeutic liquid outlet 1850 can be connected with the output port of the therapeutic liquid delivery channel 1840. The output port of the therapeutic liquid outlet 1850 can be directed outward from the ophthalmic liquid delivery ring 1800 and can include a one way valve, such that the therapeutic liquid can flow through the output port to the outside of the ophthalmic liquid delivery ring 1800.

The input port of the therapeutic liquid delivery channel 1840 can be connected to a pressure port of the pressure chamber 1830. A movable barrier 1860 is disposed within the therapeutic liquid delivery channel 1840. In an idle or non-operational state (e.g., after manufacturing and prior to operation), the movable barrier 1860 sits at the interconnection between the pressure port of the pressure chamber 1830 and the input port of the therapeutic liquid delivery channel 1840. A first end of the movable barrier 1860 is directed toward the pressure chamber 1830. A second, opposite end is directed away from the pressure chamber 1830 toward the interior volume of the therapeutic liquid delivery channel 1840 (or, equivalently, toward the therapeutic liquid outlet 1850).

Generally, the therapeutic liquid delivery channel 1840 can have a cross section (e.g., a circular cross section with a diameter within a range of 0.1 and two millimeters). The movable barrier 1860 has the same cross section (e.g., can be a spherical bead with the same diameter). Further, the cross section of the movable barrier 1860 can be larger than a cross section of an opening or a pore in the therapeutic liquid outlet 1850 through which the therapeutic liquid is delivered. In this way, the movable barrier is not delivered through the therapeutic liquid outlet 1850 upon the delivery of all of the originally stored therapeutic liquid. In an example, the movable barrier 1860 can be a solid object, like a glass bead, or a sponge like material that is saturated with a liquid. In another example, the movable barrier 1860 can be a liquid having a high viscosity (e.g., larger than a predefined viscosity threshold) or a viscosity higher than that of therapeutic liquid. In this example, the movable barrier 1860 can be silicone oil. For instance, the movable barrier 1860 can be a liquid that is not miscible, such as silicone oil.

In operation, a pressure source in the pressure chamber 1830 can be activated (e.g., based on chemical decomposition or a phase change, as illustrated in connection with FIGS. 8 and 9). The pressure source releases pressure that exerts a force on the first end of the movable barrier 1860. When this force is greater than the opposite force on the second, opposite end of the movable barrier 1860, the movable barrier 1860 travels through the therapeutic liquid delivery channel 1840, thereby causing a flow of the therapeutic liquid towards the therapeutic liquid outlet 1850, resulting in a delivery of a portion of the therapeutic liquid through the therapeutic liquid outlet 1850.

Similar to the various embodiments described in connection with FIGS. 6, 8, 9, and 11-17, the ophthalmic liquid delivery ring 1800 can include one or more flow restrictors (e.g., within or connected to the therapeutic liquid delivery channel 1840 or the therapeutic liquid outlet 1850), one or more valves (e.g., a one way valve in the therapeutic liquid outlet 1850). In addition, the ophthalmic liquid delivery ring 1800 can include a plurality of pressure chambers, a plurality of therapeutic liquid delivery channels, and/or a plurality of therapeutic liquid outlets in one-to-one, one-to-many, or many-to-many configurations. When multiple therapeutic liquid delivery channels are used, each of such channels can store a same or a different type of therapeutic liquid, and the different therapeutic liquids can be delivered at the same time or at different times and separately or as a mixed solution.

The therapeutic liquid delivery channel 1840 can have any shape and size depending on the targeted storage volume for a therapeutic liquid. For instance, the therapeutic liquid delivery channel 1840 can have a spiral shape as illustrated in FIG. 18, where the cross section of the liquid delivery channel 1840 is uniformly circular with a diameter between 0.1 and two millimeters. Other geometries of the therapeutic liquid delivery channel 1840 are possible, such as one that is circular but with a diameter that decreases in size towards the therapeutic liquid outlet 1850. Other of the therapeutic liquid delivery channel 1840 are also possible, such as a serpentine shape or a straight line.

In an example, a flow restrictor can be contained within the therapeutic liquid delivery channel 1840. For instance, the flow restrictor is implemented as dissolvable barriers that control release of a predetermined volume of fluid by blocking the therapeutic liquid within the therapeutic liquid delivery channel 1840. After an amount of time, each barrier dissolves, allowing for free flow of the therapeutic liquid through the therapeutic liquid delivery channel 1840 and out through the therapeutic liquid outlet 1850.

Figure 19:
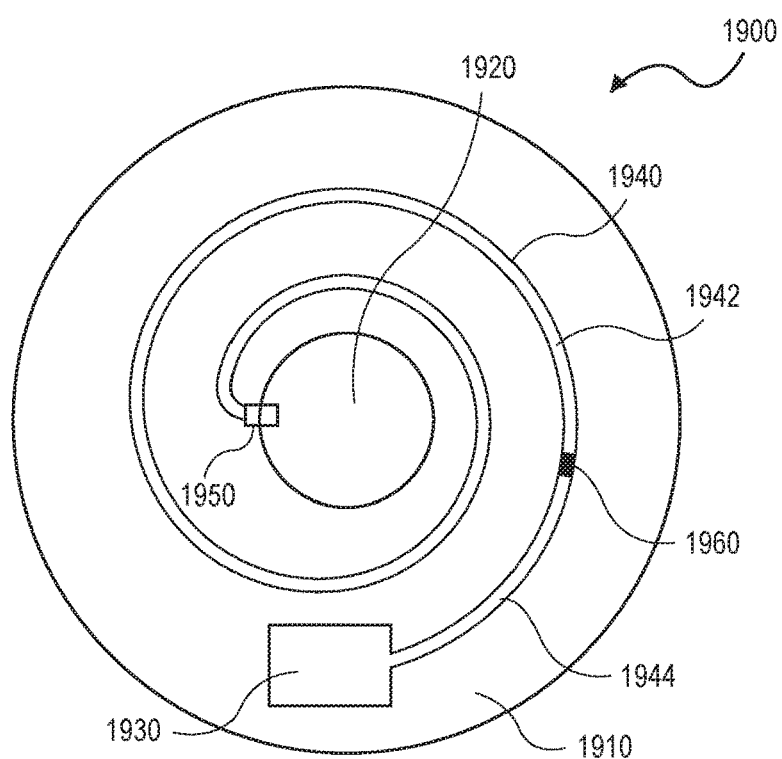
FIG. 19 illustrates a top view of another example ophthalmic liquid delivery ring that includes delivery channel in accordance with an embodiment.

FIG. 19 illustrates a top view of another example ophthalmic liquid delivery ring 1900 that includes delivery channel in accordance with an embodiment. The ophthalmic liquid delivery ring 1900 is an example of the ophthalmic liquid delivery ring 100 of FIG. 1. In addition, the ophthalmic liquid delivery ring 1900 is similar to the ophthalmic liquid delivery ring 1800 of FIG. 18 by including a pressure chamber 1930, a therapeutic liquid delivery channel 1940, a therapeutic liquid outlet 1950, and a movable barrier 1960. Similarities between the two rings are not repeated herein in the interest of brevity.

However, a difference over the ophthalmic liquid delivery ring 1800 of FIG. 18 is that, in an idle or non-operational state, the movable barrier 1960 is not originally positioned at the connection between the pressure chamber 1930 and the therapeutic liquid delivery channel 1940. Instead, the original position of the movable barrier 1960 is within the therapeutic liquid delivery channel 1940 at some distance away from the pressure source 1930. In this way, the movable barrier 1960 divides the therapeutic liquid delivery channel 1940 into two portions. The second portion 1942 is connected to the therapeutic liquid outlet 1950 and contains therapeutic liquid. The second portion 1944 is connected to the pressure chamber 1930 and does not contain therapeutic liquid. In other words, the pressure chamber 1930 includes the second portion 1944 of the therapeutic liquid delivery channel 1940.

In an example, the ophthalmic liquid delivery ring 1900 includes an annular body 1910 and an optical zone 1920. The optical zone 1920 is at the center of the annular body 1910. The annular body 1910 contains the pressure chamber 1930, the therapeutic liquid delivery channel 1940, the therapeutic liquid outlet 1950, and the movable barrier 1960. The pressure chamber 1930 is connected to one end of the therapeutic liquid delivery channel 1940. The therapeutic liquid outlet 1950 is connected to another end of the therapeutic liquid delivery channel 1940. The movable barrier 1960 is disposed within the therapeutic liquid delivery channel 1940.

In some of the above embodiments, a pressure chamber is used, whereby a generated pressure causes a flow of therapeutic liquid from a therapeutic liquid storage chamber or from a therapeutic liquid delivery channel. In particular, the generated pressure actuates a flexible membrane or a movable barrier to then cause a push or a draw of the therapeutic liquid. To direct the pressure towards the flexible membrane or the movable barrier and avoid a ballooning of any of the top surface or bottom surface of the ophthalmic liquid delivery ring by the pressure chamber, the therapeutic liquid storage chamber, the therapeutic liquid delivery channel (as applicable), pillars can be used to retain the general curvatures of the top surface and bottom surface. For example, at least one pillar is attached to both surfaces by having one end attached to the bottom surface and an opposite end attached to the top surface. The pillar can be made out of rigid or non-expandable, low elasticity material such as, for instance, glass. Multiple pillars can be used and defined as columns between the top surface and bottom surface. Other types of pillars are also possible. For instances, walls of the therapeutic liquid storage chamber, the therapeutic liquid delivery channel (as applicable) between the top surface and bottom surface can be made out of the same material to act as pillars.

Figure 20:
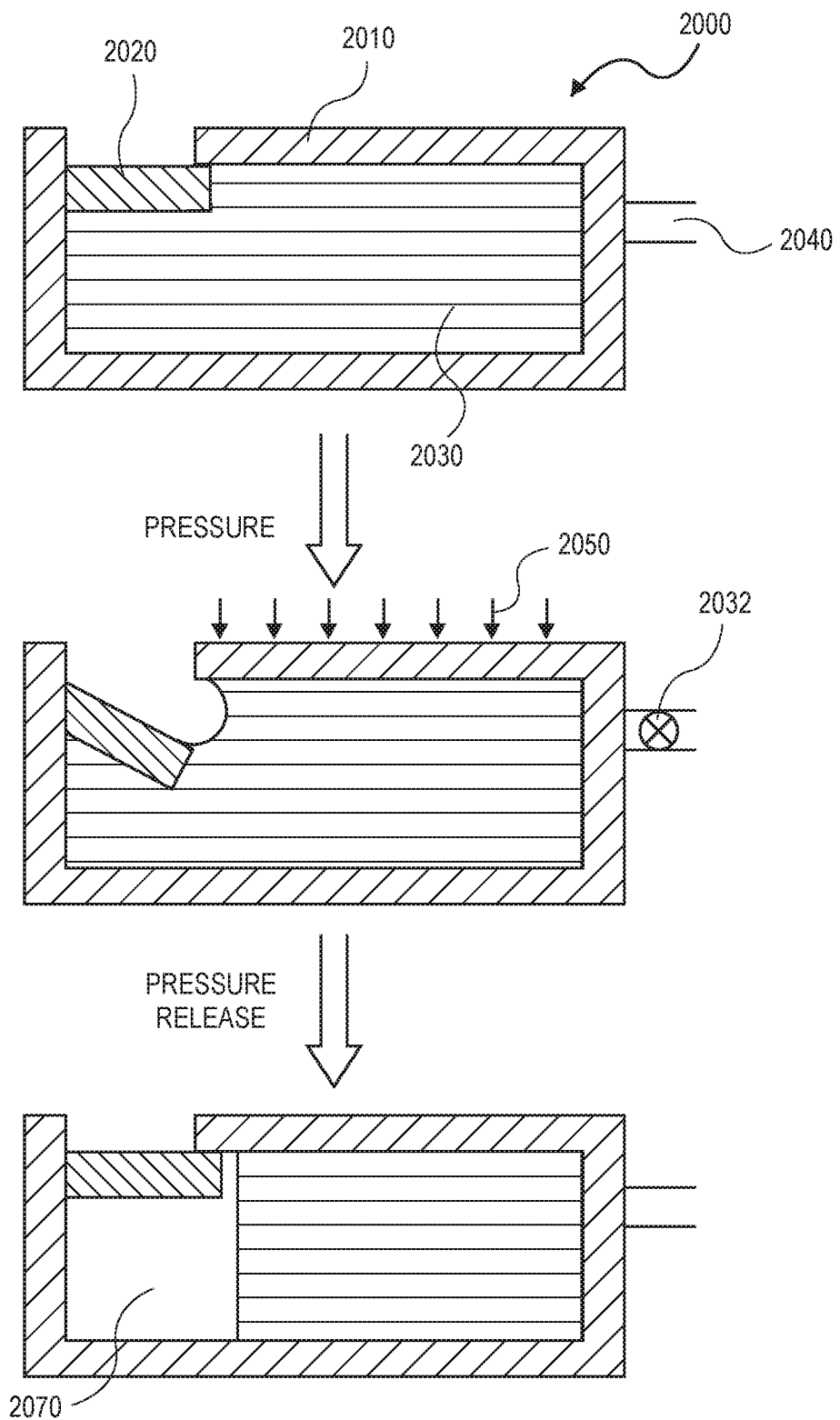
FIG. 20 illustrates an arrangement of an ophthalmic liquid delivery ring that is operated according to an external pressure source in accordance with an embodiment.

FIG. 20 illustrates an arrangement of an ophthalmic liquid delivery ring 2000 that is operated according to an external pressure source in accordance with an embodiment. The ophthalmic liquid delivery ring 2000 is an example of the ophthalmic liquid delivery ring 100 of FIG. 1. The shown arrangement illustrates a cross section of a portion of the ophthalmic liquid delivery ring 2000.

Generally, the ophthalmic liquid delivery ring 2000 is usable to pump based on external pressure on the ophthalmic liquid delivery ring 2000. The external pressure can be created by the physiological action of closing and opening the eyelid or on a finger press on the outside of the eyelid. The application of the external pressure increases pressure on the ophthalmic liquid delivery ring 2000. This pressure increase releases therapeutic liquid inside the ophthalmic liquid delivery ring 2000 as a therapeutic liquid storage chamber 2030 deforms. When the external pressure is released (e.g. the eyelid opens or the finger is removed), the therapeutic liquid storage chamber 2030 returns to its normal shape, thereby creating a vacuum that sucks the therapeutic liquid back into the therapeutic liquid storage chamber 2030. To prevent this undesired effect, a one way check valve opens relieving pressure in the ophthalmic liquid delivery ring 2000. After an inert gas or an inert liquid (e.g., air or silicone oil) is introduced to equal the displaced therapeutic liquid, the one way valve closes. Such ophthalmic liquid delivery ring 2000 need not use an internal pressure source or pressure chamber. This would be of particular interest in dry eye, where the individual would normally blink to attempt to alleviate the dryness. If gas is introduced through a port for the pressure equalization, an inert liquid of high viscosity or viscosity larger than that of the therapeutic liquid can be added near the port as to act as a barrier between the therapeutic liquid and the introduced gas. Here also, pillars can be used to retain the general curvature of the ophthalmic liquid delivery ring 2000.

The ophthalmic liquid delivery ring 2000 includes an annular body 2010 and an optical zone. The optical zone is at the center of the annular body 2010. The annular body 2010 can have the same or similar dimensions and geometries and use the same or similar material(s) as the annular body 702 of FIG. 7. Such similarities are not repeated herein. Further, the annular body 2010 contains a therapeutic liquid storage chamber 2030 that stores therapeutic liquid and a therapeutic liquid outlet 2040 coupled (e.g., connected directly or indirectly via a delivery channel and/or a flow restrictor) with the therapeutic liquid storage chamber 2030 and disposed within the inner perimeter, the outer perimeter, or the bottom surface of the annular body. In addition, the annular body 2010 includes a one way inlet valve 2020 coupled with the therapeutic liquid storage chamber 2030 and having an outlet port directed inward to the therapeutic liquid storage chamber 2030 (e.g., to the internal volume of this chamber 2030).

In addition, the annular body 2010 includes a one way outlet valve coupled with the therapeutic liquid storage chamber 2030 and having an outlet port directed outward from the therapeutic liquid storage chamber 2030 towards the therapeutic liquid outlet 2040. The one way outlet valve can be disposed within the therapeutic liquid outlet 2040 or a delivery channel between the therapeutic liquid outlet 2040 and the therapeutic liquid storage chamber 2030. For instance, the one way outlet valve is connected to an output port of the therapeutic liquid storage chamber 2030.

In comparison, the one way inlet valve 2020 is connected to an input port of the therapeutic liquid storage chamber 2030. Additionally, the annular body 2010 includes a replenishment chamber storing the inert gas or the inert liquid. In this configuration, the one way inlet valve 2020 is disposed between the replenishment chamber and the therapeutic liquid storage chamber 2030.

In an example, the one way inlet valve 2020 closes any opening between the replenishment chamber and the therapeutic liquid storage chamber 2030 in a state where no external pressure is applied (e.g., a no pressure state). In a pressure state (e.g., when the external pressure is applied to the annular body 2010), at least the top surface of the annular body 2010 actuates (e.g., bows in, where this top surface is in contact with the eyelid). This actuation causes a pressure on the therapeutic liquid storage chamber 2030 (shown with the vertical down arrows 2050 in FIG. 20), thereby causing a portion 2032 of the therapeutic liquid to flow out from the therapeutic liquid storage chamber 2030 and towards the therapeutic liquid outlet 2040. In parallel, the pressure change actuates the one way inlet valve 2020 to draw replenishment material (e.g., inert gas or inert liquid) from the replenishment chamber in to the therapeutic liquid storage chamber 2030. Upon a return to the no pressure state (e.g., a pressure release), the one way inlet valve 2020 is closed. The introduced replenishment material 2070 stays in the therapeutic liquid storage chamber 2030, thereby avoiding the portion 2032 of the therapeutic liquid to be sucked back into the therapeutic liquid storage chamber 2030. In addition, if a one way outlet valve is connected to an output port of the therapeutic liquid storage chamber 2030 and having a flow direction towards the therapeutic liquid outlet 2040, additional protection can be built into the annular body 2010 to avoid the return of the portion 2032 into the therapeutic liquid storage chamber 2030.

Figure 21:
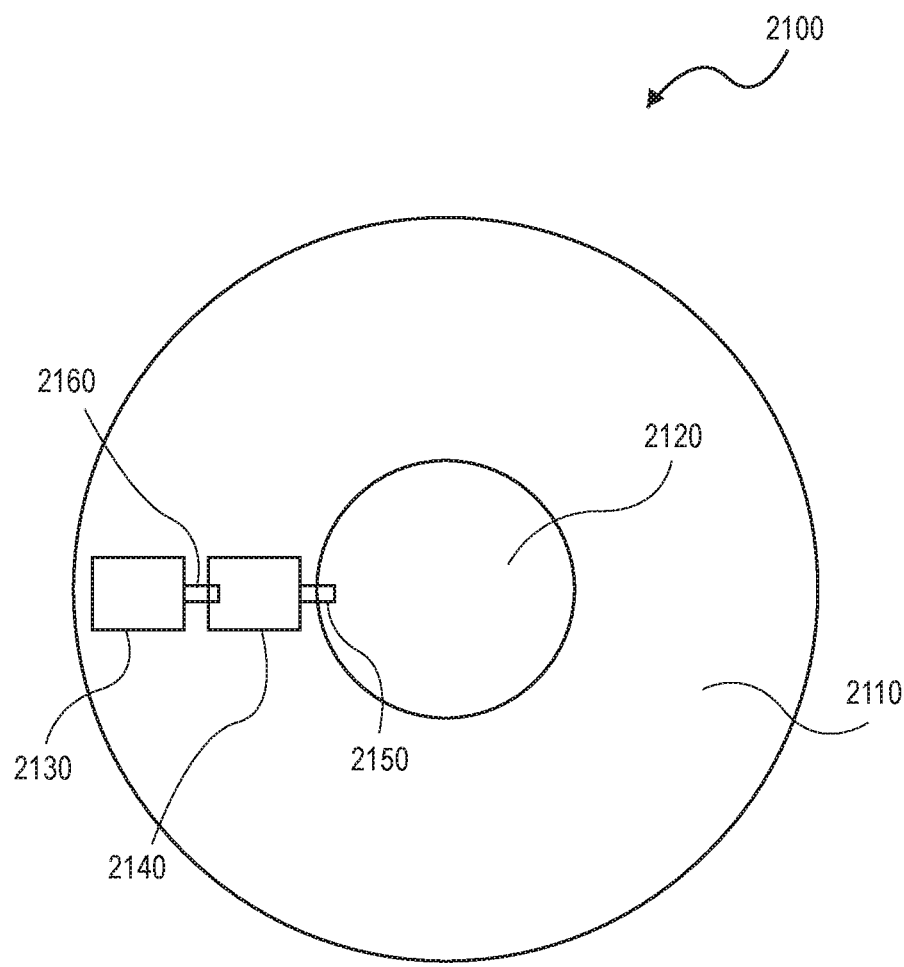
FIG. 21 illustrates a top view of an ophthalmic liquid delivery ring that is operated according to an external pressure source in accordance with an embodiment.

FIG. 21 illustrates a top view of an ophthalmic liquid delivery ring 2100 that is operated according to an external pressure source in accordance with an embodiment. The ophthalmic liquid delivery ring 2100 is an example of the ophthalmic liquid delivery ring 2100 of FIG. 20.

In an example, the ophthalmic liquid delivery ring 2100 includes an annular body 2110 and an optical zone 2120. The optical zone 2120 is at the center of the annular body 2110. The annular body 2110 contains a replenishment chamber 2130, a therapeutic liquid storage chamber 2140, a therapeutic liquid outlet 2150, and a one way inlet valve 2160.

The replenishment chamber 2130 can occupy a portion of the volume within the ophthalmic liquid delivery ring 2100, whereas the therapeutic liquid storage chamber 2140 occupies a second or a remaining portion of the volume. Similarly to the embodiments described in connection with FIGS. 11-13, the portion occupied by the replenishment chamber 2130 can be similar to the portion occupied by any of the pressure chambers described in these figures. And the portion occupied by the therapeutic liquid storage chamber 2140 can be similar to the portion occupied by any of the therapeutic liquid storage chambers described in these figures. The replenishment chamber 2130 stores a replenishment material. The therapeutic liquid storage chamber 2140 stores therapeutic liquid.

The one way inlet valve 2160 can connect the replenishment chamber 2130 with the therapeutic liquid storage chamber 2140. The flow direction of the one way inlet valve 2160 can be outward from the replenishment chamber 2130 and toward the therapeutic liquid storage chamber 2140. In this way and upon an activation of the one way inlet valve 2160, a portion of the replenishment material can flow from the replenishment chamber 2130 into the therapeutic liquid storage chamber 2140.

The therapeutic liquid outlet 2150 can be coupled with the therapeutic liquid storage chamber 2140. The coupling can be direct (e.g., an output port of the therapeutic liquid storage chamber 2140 is connected to an input port of the therapeutic liquid outlet 2150). The coupling can alternatively be indirect through a delivery channel, a flow restrictor, and/or a one way valve. If a one way valve is used, this valve is referred to herein as a one way outlet valve to denote that the flow direction is outward from the therapeutic liquid storage chamber 2140 and toward the therapeutic liquid outlet 2150.

Other variations to the ophthalmic liquid delivery ring 2100 are also possible, similar to the variations of the ophthalmic liquid delivery rings described in connection with FIGS. 1-19. For example, a therapeutic liquid delivery channel can be used instead of a therapeutic liquid storage chamber. In addition, the ophthalmic liquid delivery ring 2100 can include a plurality of replenishment chambers, a plurality of therapeutic liquid storage chambers/delivery channels, and/or a plurality of therapeutic liquid outlets in one-to-one, one-to-many, or many-to-many configurations. When multiple therapeutic liquid storage chambers/delivery channels are used, each of such storage chambers/delivery channels can store a same or a different type of therapeutic liquid, and the different therapeutic liquids can be delivered at the same time or at different times and separately or as a mixed solution.

Other variations to the ophthalmic liquid delivery rings described in connection with FIGS. 1-21 are also possible. For example, an ophthalmic liquid delivery ring includes the same components as the ophthalmic liquid delivery ring 700 except for a flexible membrane between a pressure chamber and a therapeutic liquid storage chamber. In this example variation, a moveable barrier can be positioned between the pressure chamber and the therapeutic liquid storage chamber similarly to the positioning of a movable barrier between a pressure chamber and a therapeutic liquid delivery channel as in FIGS. 18 and 19. Alternatively, no movable barrier is moved. Instead, upon activation of a pressure source in the pressure chamber, the pressure source (e.g., the released gas molecules) becomes in direct contact with a therapeutic liquid contained in the therapeutic liquid storage chamber. A similar alternative can be used in an ophthalmic liquid delivery ring that includes a pressure chamber and a therapeutic liquid delivery channel as in FIGS. 18 and 19. In particular, no movable barrier may be needed. Instead, upon activation of a pressure source in the pressure chamber, the pressure source becomes in direct contact with a therapeutic liquid contained in the therapeutic liquid delivery channel. In both of these two alternatives that do not use a movable barrier, the interface between the pressure chamber and therapeutic liquid storage chamber or the therapeutic liquid delivery channel (e.g., an output port of the pressure chamber or an input port of the therapeutic liquid storage chamber or the therapeutic liquid delivery channel) can include the pressure source or a frangible material that can be broken upon the activation of the pressure source. Or this interface can include a one way valve directed outward from the pressure chamber such that, upon activation of the pressure source, the released gas molecules flow out from this pressure chamber.

In an example, pressure can also be generated by heating with a laser before insertion to decompose a compound. Ammonium nitrite is an example substance, which would decompose into $N_2$ and $H_2O$ under heat ($NH_4NO_3 \rightarrow N_2O + 2H_2O$).

In another example, the decomposition of water into in $H_2$ and $O_2$ gases by electrolysis is possible, where the decomposition relies on an inductively coupled coil and coupling capacitor powered by a primary coil. This can be powered daily or be done just before an ophthalmic liquid delivery ring is placed on the eye, by putting the ophthalmic liquid delivery ring over the coil after removing from the casement. A membrane containing the salt solution can be isolated from the therapeutic liquid.

In an additional example, the therapeutic liquid storage chamber can be initially loaded under positive hydraulic pressure with flow out of the channel controlled by a gated valve (e.g. by means of a temperature sensitive polymer). Similarly, a therapeutic liquid storage chamber can be initially loaded under negative pressure to draw therapeutic liquid out of another therapeutic liquid storage chamber.

In an example, storage chambers, channels, and compartments can be filled with therapeutic liquid, other liquids, and/or components through a batch filling method to obviate the need to fill each ophthalmic liquid delivery ring individually. For example, ophthalmic liquid delivery rings can be submerged in the desired therapeutic liquid to be introduced, a vacuum can be pulled to remove gas from the channels and then pressure can be restored (sub-atmospheric, atmospheric, or supra-atmospheric) at which point the therapeutic liquid will enter the voids.

In yet another example, thermal sensitive polymers can also be used to create both positive and negative pressure sources. In one illustration, a pair of materials with different thermal expansion properties are bonded into a diaphragm over a storage chamber. Upon temperature change, the differential thermal stresses result in a deflection of the diaphragm leading to either a volume increase (pressure decrease) or volume decrease (pressure increase), depending on the relative orientation of the membrane. This effect can be amplified by utilizing thermally responsive materials with a phase change between storage temperature and eye temperature. The same principle can be used, but with materials possessing different sensitivity (e.g. pH, light, moisture). The positive pressure can be used to push therapeutic liquid out of the ophthalmic liquid delivery ring, open a valve, or close a valve; the negative pressure can be used to draw therapeutic liquid out of a storage chamber (e.g. pulling it out from an impermeable reservoir over a semi-permeable region), open a valve, or close a valve.

In a further example, a means for generating pressure is to fill a storage chamber with a hypertonic solution or hygroscopic material such that it swells from moisture in the eye. The swelling can be used to displace therapeutic fluid or operate a valve. Zero order kinetics can be achieved by designing the membrane of the storage chamber such that transport of water into it is diffusion limited, thereby achieving a constant rate of swelling, which can be transduced into a constant rate of therapeutic liquid delivery.

In addition, various techniques are possible to keep an ophthalmic liquid delivery ring dormant (e.g., inactive) until operation (e.g., being placed or about to be placed on an eye). The techniques to keep the drug from exiting the ophthalmic liquid delivery ring dormant before application—keeping it dormant—can be divided into techniques incorporated into the packaging, and techniques incorporated into the ophthalmic liquid delivery ring.

In one example of a technique incorporated into the packaging, a spring clip can be added to the casement which applies pressure to the contact on one or multiple channels squeezing them shut. This could be done on the therapeutic liquid outlet of the ophthalmic liquid delivery ring, or to separate the pressure chamber from the therapeutic liquid with a channel, or to separate two reactive substances from each other that, if mixed, generate an expanding gas of solid (such as separating peroxide from platinum).

In another example of a technique incorporated into the packaging, if using a phase changing material in a pressure source, such as perfluoropentane or Freon-22, the ophthalmic liquid delivery ring may be cooled to the point that the vapor pressure is below one atmosphere. Storing it at low temperatures would therefore prevent a phase change pressure source from being active. For a gaseous pressure source, the same may be done at a lower temperature.

In a further example of a technique incorporated into the packaging, temperature sensitive materials (e.g. Poly(N-isopropylacrylamide) or pairs of materials with different thermal expansion coefficients (e.g. in a biomaterial strip) can be utilized to seal or gate a therapeutic liquid storage chamber at room temperature, but open at eye temperature.

In yet another example technique incorporated into the packaging, for an ophthalmic liquid delivery ring with a pressure chamber that relies on a fluidic resistor to regulate the flow can be stored in a package with an elevated internal pressure that matches the source's pressure. Similar to a soda can, opening the casement would bring this ring to atmospheric pressure and the newly formed pressure differential between the pressure source and atmosphere will initiate flow.

In an example of a technique incorporated into an ophthalmic liquid delivery ring, the flow of the therapeutic liquid can be initiated by removing some form of a stop in the ophthalmic liquid delivery ring itself. Dissolvable plugs are possible. In such a case, a laser can be used to melt a nanoparticle impregnated plug, such as paraffin with iron nanoparticles. Before placing on the eye, a laser would selectively melt the plug by heating the nanoparticles. Since the heated area would be small, and the entire ophthalmic liquid delivery ring would not be heated (the laser would only act on the plug itself), the thermal mass of the plug would be low enough that the ophthalmic liquid delivery ring would be safe to handle immediately following laser application.

In another example of a technique incorporated into an ophthalmic liquid delivery ring, a low melting temperature hydrogel (e.g. agarose) can be used to occlude the therapeutic liquid outlet or the flow path, maintaining the therapeutic liquid within the ophthalmic liquid delivery ring until placed in contact with the warm eye. Alternatively, a temperature sensitive material (e.g., Poly(N-isopropylacrylamide)) can be placed in the flow path, thereby maintaining a swollen occlusion at storage temperatures, but contracting at body temperature to open up the flow path and allow for liquid flow. In both cases, the temperature sensitive polymers can alternatively be used to hold a valve in a closed position and allow it to open upon increased temperature.

In a further example of a technique incorporated into an ophthalmic liquid delivery ring, a material that is dissolvable in tears, but otherwise possesses the properties to occlude the flow path or hold a valve (e.g. a solid or gel) can also be used (e.g. salt, sugar, metals). In some cases, where the contact of the dissolvable material with the therapeutic drug would lead to dissolution during storage, the contacting face can be coated with a thin layer of impermeable material to prevent this. Upon introduction into the eye, the exposed face can dissolve leaving the thin layer of impermeable material in its place. By choosing the mechanical properties of this thin layer appropriately, it can be designed to rupture without the mechanical support of the dissolvable material, thereby allowing for operation or a valve or opening of the flow path. A degradable material can also be utilized (in place of a dissolvable material), which in some instances, can obviate the need for an impermeable layer of material. For instance, a material susceptible to degradation by an enzyme (e.g. protease) in tears can be used as it will selectively degrade in the eye, but not in the packaging.

In an example of a technique incorporated into both the packaging and an ophthalmic liquid delivery ring, it is also possible to use a magnet on the packaging, whereby removing the ophthalmic liquid delivery ring from the packaging would open an outlet. Multiple approaches are possible to implement this technique. One approach would be that there is a magnetically responding flap sealing over an outlet. This could simply be a polymer embedded with magnetic particles or magnetic stainless steel sheet, which would be pulled down by the magnet in the packaging, sealing a channel shut. It would also be possible to use a small moveable ball as a plug, and have the action of removing the ophthalmic liquid delivery ring from the package move the magnet so it no longer seals an outlet port.

In an additional example, pressure-producing substances, pressurized source, or propellant can be contained within a brittle reservoir or behind a brittle seal. By bending an ophthalmic liquid delivery ring, the seal will crack while not producing sharp edges. This would allow the contained substance, to be released and act as designed (whether act directly to push on therapeutic liquid or mix with another substance to generate pressure). A crystallized parylene bag is an example of a brittle material that can be formed into a seal or reservoir, but would be unable to tear a contact lens.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" and "substantially" in reference to a diameter, radius, height, volume, or irradiance, wavelength, or other engineering units include measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The abstract of the disclosure is provided to allow the reader to quickly ascertain the nature of the technical disclosure. It is submitted with the understanding that it will not be used to interpret or limit the scope or meaning of the claims. In addition, in the foregoing detailed description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separately claimed subject matter.

What is claimed is:

1. An ophthalmic liquid delivery contact lens apparatus wearable on a sclera of an eye, the eye treatment apparatus comprising:
    a contact lens annular body defining a hollow optical zone, wherein:
        the annular body is defined by an inner perimeter, an outer perimeter that surrounds the inner perimeter, a top surface between the inner perimeter and the outer perimeter, and a bottom surface opposite the top surface,
        the inner perimeter surrounds the hollow optical zone, and
        a shortest distance between two opposite points of the inner perimeter is between eight and twelve millimeters;
    a therapeutic liquid storage chamber disposed within the annular body;
    a therapeutic liquid outlet coupled with the therapeutic liquid storage chamber and disposed within the inner perimeter, the outer perimeter, or the bottom surface;
    a therapeutic liquid delivery channel disposed within the annular body and having one end connected to the therapeutic liquid storage chamber and an opposite end connected to the therapeutic liquid outlet; and
    a pressure chamber disposed within the annular body and coupled with the therapeutic liquid delivery channel,
    wherein the therapeutic liquid outlet is sized and configured to deliver a therapeutic liquid outside of the annular body,
    wherein the therapeutic liquid storage chamber comprises a therapeutic liquid for an eye,
    wherein the inner perimeter is centered around a center of the hollow optical zone, wherein the outer perimeter is centered around the center of the hollow optical zone and has a diameter between twenty and one hundred millimeters.

2. The ophthalmic liquid delivery contact lens apparatus of claim 1, further comprising a plurality of therapeutic liquid storage chambers, each of the plurality of therapeutic liquid storage chambers coupled with the therapeutic liquid outlet.

3. The ophthalmic liquid delivery contact lens apparatus of claim 1, further comprising a plurality of therapeutic liquid storage chambers and a plurality of therapeutic liquid outlets, each of the plurality of therapeutic liquid storage chambers coupled with a separate one of the plurality of therapeutic liquid outlets.

4. The ophthalmic liquid delivery contact lens apparatus of claim 1, further comprising a plurality of therapeutic liquid outlets, each of the plurality of therapeutic liquid outlets coupled with the therapeutic liquid storage chamber.

5. The ophthalmic liquid delivery contact lens apparatus of claim 1, further comprising a pillar having one end attached to the bottom surface and an opposite end attached to the top surface.

6. The ophthalmic liquid delivery contact lens apparatus of claim 1, further comprising a one way valve disposed within the delivery channel or the therapeutic liquid outlet.

7. The ophthalmic liquid delivery contact lens apparatus of claim 1, further comprising a flow restrictor disposed within or connected to the therapeutic liquid delivery channel or the therapeutic liquid outlet.

* * * * *